US007743770B2

(12) United States Patent
Curti et al.

(10) Patent No.: US 7,743,770 B2
(45) Date of Patent: Jun. 29, 2010

(54) NASAL AND ORAL CANNULA HAVING THREE OR MORE CAPABILITIES AND METHOD OF PRODUCING SAME

(75) Inventors: James N. Curti, Bakersfield, CA (US); Kyle L. Adriance, Bakersfield, CA (US); Russell J. Kinney, Wofford Heights, CA (US)

(73) Assignee: Salter Labs, Arvin, CA (US)

( * ) Notice: Subject to any disclaimer, the term of this patent is extended or adjusted under 35 U.S.C. 154(b) by 1134 days.

(21) Appl. No.: 11/272,348

(22) Filed: Nov. 10, 2005

(65) Prior Publication Data

US 2006/0174886 A1 Aug. 10, 2006

Related U.S. Application Data

(60) Continuation-in-part of application No. 11/011,012, filed on Dec. 13, 2004, which is a continuation-in-part of application No. 10/265,527, filed on Oct. 4, 2002, now Pat. No. 6,830,445, which is a division of application No. 09/883,843, filed on Jun. 18, 2001, now Pat. No. 6,533,984, which is a continuation-in-part of application No. 09/754,471, filed on Jan. 4, 2001, now Pat. No. 6,533,983.

(51) Int. Cl.
*A61M 15/08* (2006.01)
*A62B 7/00* (2006.01)

(52) U.S. Cl. .............................. 128/207.18; 128/204.18; 128/200.24; 128/204.12; 128/206.18; 128/207.13; 128/912; 128/DIG. 26; 128/206.11; 128/207.14; 604/94.01; 604/275; 604/533; 604/284

(58) Field of Classification Search ............ 128/204.18, 128/207.18, 200.24, 204.12, 206.18, 207.13, 128/912, DIG. 26, 206.11, 207.14; 604/94.01, 604/275, 533, 284
See application file for complete search history.

(56) References Cited

U.S. PATENT DOCUMENTS 2,053,357 A 9/1936 Winder (Continued)

FOREIGN PATENT DOCUMENTS

EP 0 993 094 4/2000

(Continued)

OTHER PUBLICATIONS

Salter Labs, "Dual Oral/Nasel ETCO2 Sampling Cannulas", Copyright 1991, revised Sep. 2003.

*Primary Examiner*—Patricia M Bianco
*Assistant Examiner*—Nihir Patel
(74) *Attorney, Agent, or Firm*—Davis & Bujold, P.L.L.C.

(57) ABSTRACT

A cannula having at least three separate flow passages and comprising separate nasal and mouth main bodies. The nasal body has first and second nares and first and second main flow chambers respectively communicating with first and second ports, and the first and second flow chambers are separated from one another by a septum. The mouth main body is adjacent the nasal main body and has at least one mouthpiece and at least a third main flow chamber therein communicating with a third port. The cannula has at least first, second and third flow paths which can be connected with a desired supply, monitoring or detection device. The invention also relates to the method of manufacturing the cannula.

18 Claims, 21 Drawing Sheets

U.S. PATENT DOCUMENTS

| | | | |
|---|---|---|---|
| 2,296,011 A | 9/1942 | Beal | |
| 2,824,407 A | 2/1958 | Ebel | |
| 2,854,695 A | 10/1958 | Moreau | |
| 3,643,660 A | 2/1972 | Hudson et al. | |
| 3,731,900 A | 5/1973 | Havstad | |
| 3,802,431 A | 4/1974 | Farr | |
| 3,906,071 A | 9/1975 | Cook et al. | |
| 3,931,381 A | 1/1976 | Lindberg | |
| 4,106,505 A | 8/1978 | Salter et al. | |
| 4,152,688 A | 5/1979 | Dietz | |
| 4,433,219 A | 2/1984 | Dietz | |
| 4,602,643 A | 7/1986 | Dietz | |
| 4,695,241 A | 9/1987 | Ventimiglia et al. | |
| 4,745,925 A | 5/1988 | Dietz | |
| 4,800,116 A | 1/1989 | Ventimiglia et al. | |
| 4,818,320 A | 4/1989 | Weichselbaum | |
| 4,878,502 A | 11/1989 | Dietz | |
| 5,005,571 A | 4/1991 | Dietz | |
| 5,024,219 A | 6/1991 | Dietz | |
| 5,038,771 A | 8/1991 | Dietz | |
| 5,046,491 A | 9/1991 | Derrick | |
| 5,052,400 A | 10/1991 | Dietz | |
| 5,074,299 A | 12/1991 | Dietz | |
| 5,133,923 A | 7/1992 | Klug | |
| 5,335,656 A | 8/1994 | Bowe et al. | |
| 5,380,182 A | 1/1995 | Packard et al. | |
| 5,485,853 A | 1/1996 | Stubbs | |
| 5,513,634 A | 5/1996 | Jackson | |
| 5,682,881 A | 11/1997 | Winthrop et al. | |
| 5,922,365 A | 7/1999 | Reichner | |
| 6,045,514 A | 4/2000 | Raviv et al. | |
| 6,171,258 B1 | 1/2001 | Karakasoglu et al. | |
| 6,213,955 B1 | 4/2001 | Karakasoglu et al. | |
| 6,217,818 B1 | 4/2001 | Collette et al. | |
| 6,247,470 B1 | 6/2001 | Ketchedjian | |
| 6,379,312 B2 * | 4/2002 | O'Toole | 600/529 |
| 6,422,240 B1 * | 7/2002 | Levitsky et al. | 128/207.18 |
| 6,533,984 B2 * | 3/2003 | Curti | 264/219 |
| 6,635,214 B2 | 10/2003 | Rapacki | |
| 6,910,876 B2 | 6/2005 | Ainsworth et al. | |
| 2005/0051176 A1 | 3/2005 | Riggins | |

FOREIGN PATENT DOCUMENTS

| | | |
|---|---|---|
| FR | 2 197 613 | 3/1975 |
| RU | 1775957 | 9/1995 |
| RU | 1793628 | 10/1995 |

* cited by examiner

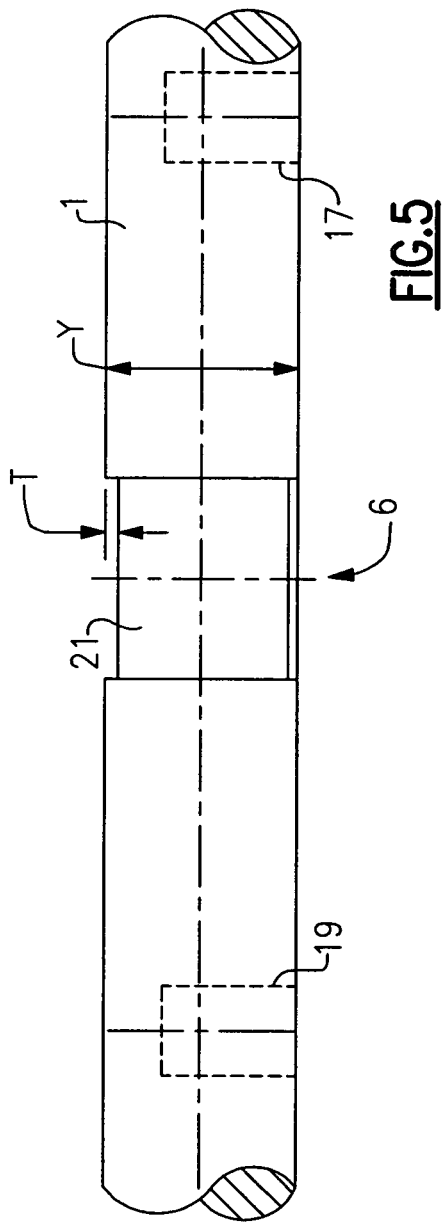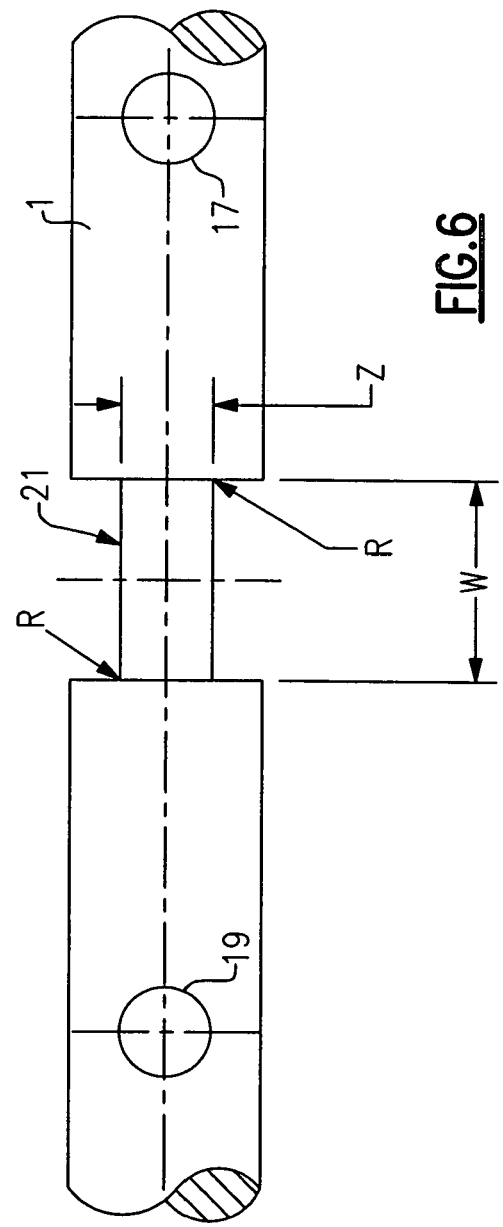

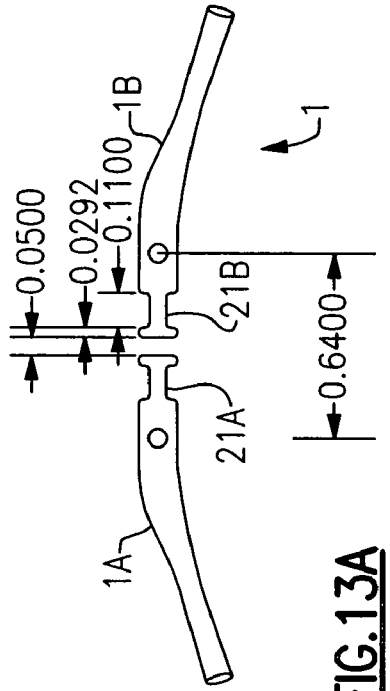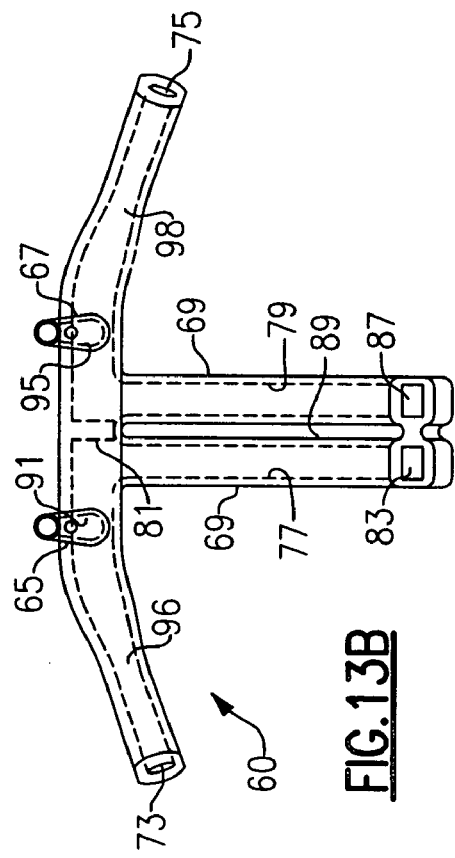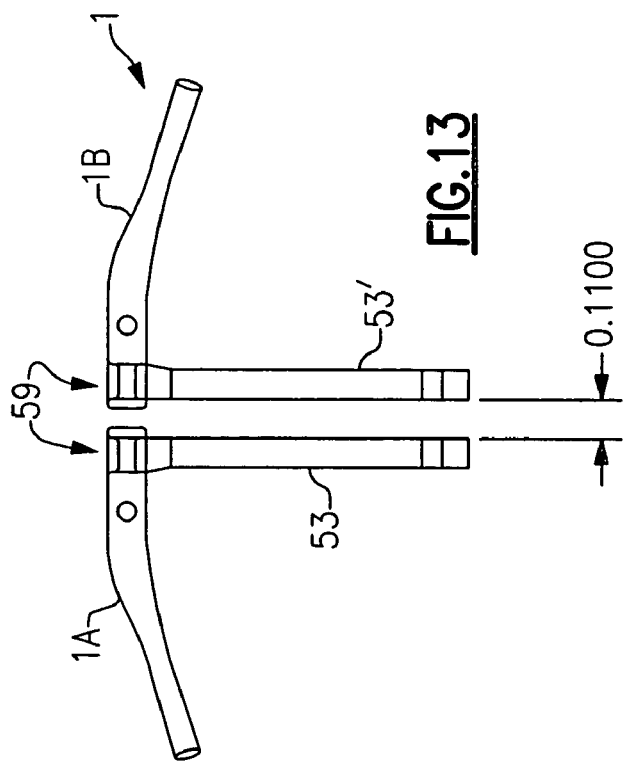
FIG.13A
FIG.13B
FIG.13

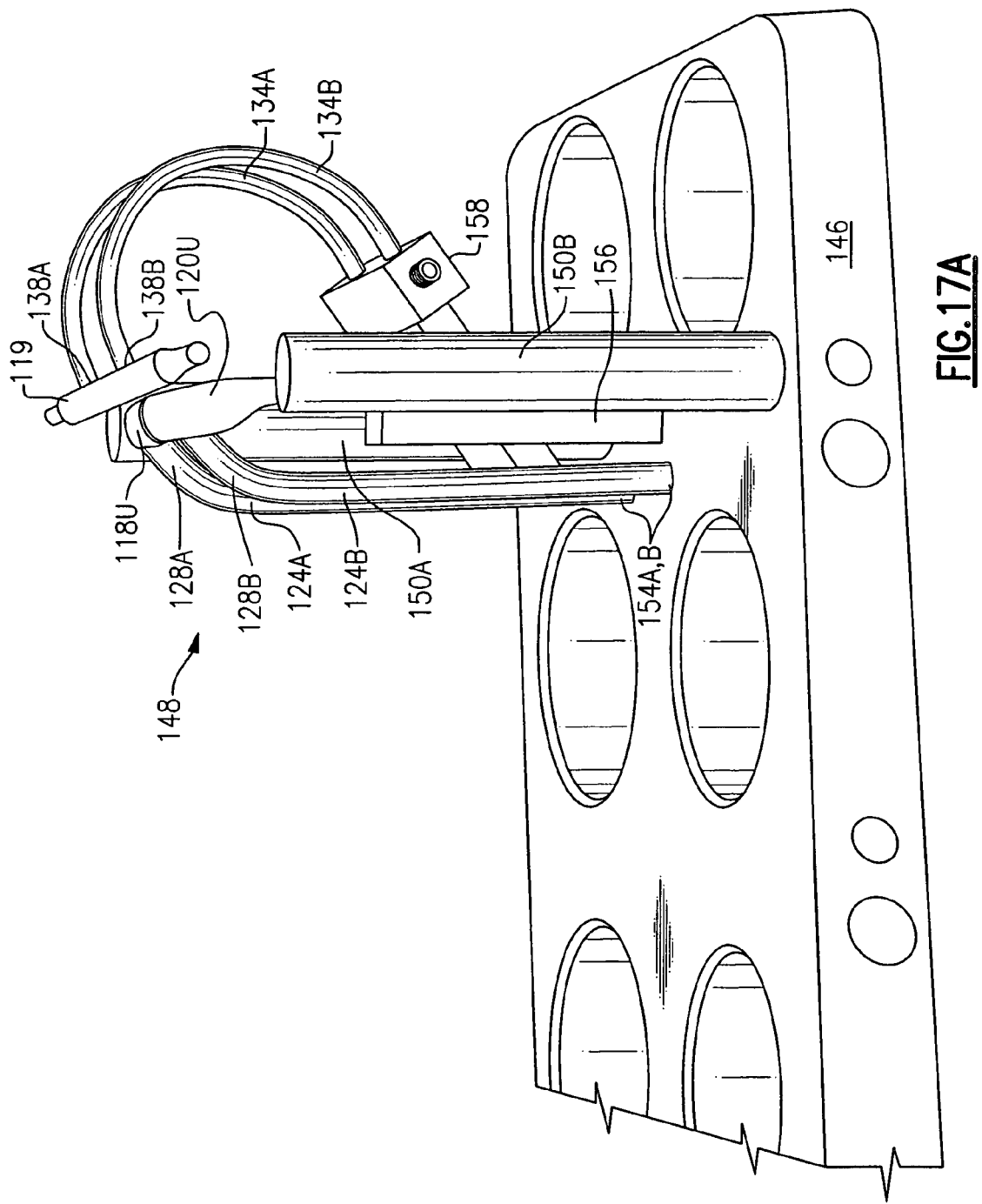

NASAL AND ORAL CANNULA HAVING THREE OR MORE CAPABILITIES AND METHOD OF PRODUCING SAME

This application is a continuation-in-part of application Ser. No. 11/011,012 filed Dec. 13, 2004, which is a continuation-in-part of application Ser. No. 10/265,527 filed Oct. 4, 2002 now U.S. Pat. No. 6,830,445, which is a divisional of application Ser. No. 09/883,843 filed Jun. 18, 2001, now U.S. Pat. No. 6,533,984, which is a continuation-in-part of application Ser. No. 09/754,471 filed on Jan. 4, 2001, now U.S. Pat. No. 6,533,983 B2.

FIELD OF THE INVENTION

This invention relates to a novel cannula which is suitable for use for both nasal and oral applications and a method of producing the cannula using disconnectable mandrel parts to form a mold over or on which the cannula forming plastics material is applied to form the cannula.

BACKGROUND OF THE INVENTION

This invention relates generally to cannulas adapted for both oral and nasal applications for monitoring breathing of a patient, sampling the end tidal $CO_2$ content in the exhaled breath of a patient to determine the patient's $CO_2$ blood concentration level, or supplying a treating gas, such as oxygen, to a patient. In addition, the invention relates to a method of manufacturing a cannula adapted to communicate with both nasal passages and the mouth of a patient for use in monitoring breathing, sampling end tidal $CO_2$, supplying a treating gas and is also suitable for the detection of apnea (the absence of breathing).

Nasal cannulas are commonly used to administer a treating gas, such as oxygen, to humans having respiratory problems. Illustrations of nasal cannulas used for this purpose are found in U.S. Pat. No. 3,802,431. Nasal cannulas have also been used for inhalation therapy, made possible by development of inhalation sensors, such as described in U.S. Pat. No. 4,745,925. A nasal cannula can be used to monitor breathing and for detection of apnea when connected to an inhalation sensor.

Nasal cannulas additionally adapted to communicate with the mouth of a patient to permit administration of a gas or sensing of apnea during periods of mouth breathing or nasal blockage are also known.

The present invention relates to a novel cannula and method of manufacturing the novel cannula having the ability to communicate with both nasal cavities as well as the mouth or oral cavity of a patient. This apparatus and method provides, in the preferred embodiment, disconnectable mandrel components which when assembled, form a mold over which a cannula forming polymeric material is applied, and which, through the capability of each mandrel component being disconnectable from the other mandrel component(s), facilitates removal of the mandrel components from the formed or manufactured cannula.

Prior art relating to dipping of a part in a plastisol to create a coating is exemplified by U.S. Pat. Nos. 3,906,071, 4,695,241 and 4,800,116, and the disclosures of those references are hereby incorporated by reference.

The closest known prior art is believed to be a sampling cannula sold under the Salter Labs "One—No. 4001 oral/nasal $CO_2$ sample line" trade designation. This cannula has a pair of prongs or sampling line(s) which each communicate with one nostril of the patient and a pair of straight prongs or sampling line(s) which both communicate with the oral or mouth cavity of the patient. A U-shaped wired is glued or otherwise affixed to the exterior surface of the main body of the cannula but the wire extends only about half the length of each of the oral or mouth cavity prongs or sampling line(s). All of the nasal and the oral and mouth prongs or sampling line(s) communicate with one another so that the cannula can only perform one function. The leading free end of the oral or mouth prongs or sampling line(s) can be bent over in front of the teeth of the patient and any excess length of the prong(s) or sampling line(s) can be trimmed. It is to be appreciated that a sidewall of each of the nares may be provided with a small opening therein to prevent occlusion of the nare during use. This is particularly important if the nare is to be used in combination with a sampling device.

SUMMARY OF THE INVENTION

It is an object of the invention to provide a method of manufacturing a cannula using an assembly of disconnectable mandrel components over which cannula forming plastics or polymeric material is applied. Application of the plastics or polymeric material over the mandrel assembly and subsequent extraction of the mandrel components from one another, following sufficient curing of the plastics or polymeric material, results in a manufactured cannula with contiguous internal flow paths for sampling the exhaled breath of a patient to detect the end tidal $CO_2$ in the blood of a patient, sensing patient breathing, and/or supplying a treating gas to the patient.

It is a further object of the invention to provide a multi-part mandrel assembly for forming a cannula which facilitates extraction of each of the mandrel assembly components following at least partial curing of the polymeric material forming the cannula.

Still another object of the invention is to form the main body forming mandrel component as two separate, slightly spaced apart components which remain spaced apart from one another by a gap or void, during the dipping process, so that the gap void becomes filled with a plastics or polymeric material to form a wall, septum or barrier which partitions or divides the internal passage of the cannula into two separate compartments or passageways, one which facilitates either sensing of patient breathing, monitoring of the end tidal $CO_2$ in a patient's blood stream or supplying a treating gas to the patient, etc., while the other of which also facilitates another function, such as, sensing of patient breathing, monitoring of the end tidal $CO_2$ in a patient's blood stream, and/or supplying a treating gas to the patient, etc.

Another object of the invention is to produce a cannula having at least one mouthpiece, and alternatively a pair of side by side mouthpieces, extending from the main body of the cannula to the patient's mouth, the cannula is provided with at least one passageway, or alternatively a pair of passageways, for supplying a gas to the patient via a demand regulator for example, or sampling a patient's oral exhalation for monitoring the end tidal $CO_2$ in a patient's blood stream for instance, and the at least one mouthpiece, or alternatively the pair of mouthpieces, has a desired curvature or orientation so that the opening of each mouthpiece is located in or adjacent the mouth or oral cavity of a patient for detecting or sensing the exhaled breath of the patient.

It is a further object of the invention to provide a nasal cannula which is continuously able to both supply and withdraw a gas sample from a mouth of a breathing patient or a patient which alternates breathing between the nose and the mouth and is also able to continuously detect breathing of a patient who alternates breathing between the nose and the mouth.

Yet another object of the invention to provide a nasal cannula which is relatively inexpensive to manufacture by a dipping process as an integral unitary cannula.

Still another object of the invention is to provide a multi-part mandrel assembly for forming a cannula which facilitates extraction of each of the mandrel assembly components following at least partial curing the polymeric material forming the cannula.

The invention also relates to a nasal cannula comprising: a hollow main body having opposed first and second ends with a first opening formed in the first end and a second opening formed in the second end, and the main body defining an internal chamber therein; a partition dividing the internal chamber into first and second flow compartments, the first flow compartment communicating with the first opening and the second flow compartment communicating with the second opening; a flow passageway of a first nasal prong communicating with the first compartment and a flow passageway of the first mouthpiece communicating with the first compartment to define a first flow path communicating with both a first nostril and a mouth of the patient; and a flow passageway of a second nasal prong communicating with the second compartment and a flow passageway of the second mouthpiece communicating with the first compartment to define a second flow path communicating with both a second nostril and the mouth of the patient.

The invention also relates to a method of using a nasal cannula comprising a hollow main body having opposed first and second ends with a first opening formed in the first end and a second opening formed in the second end, and the main body defining an internal chamber therein; a partition dividing the internal chamber into first and second flow compartments, the first flow compartment communicating with the first opening and the second flow compartment communicating with the second opening; a flow passageway of a first nasal prong communicating with the first compartment and a flow passageway of the first mouthpiece communicating with the first compartment to define a first flow path communicating with both a first nostril and a mouth of the patient; and a flow passageway of a second nasal prong communicating with the second compartment and a flow passageway of the second mouthpiece communicating with the first compartment to define a second flow path communicating with both a second nostril and the mouth of the patient, and a first end of a first tubing being connected to the first opening and a first end of a second tubing being connected to the second opening; the method comprising the steps of: placing the first and second nasal prongs in the nostrils of the patient; connecting the second end of the first tubing to one of a device for monitoring breathing of a patient, a device for sampling the end tidal $CO_2$ content in the exhaled breath of a patient to determine the patient's $CO_2$ blood concentration level, a device for supplying a treating gas to the patient and a device for detection of apnea; and connecting the second end of the second tubing to one of a device for monitoring breathing of a patient, a device for sampling the end tidal $CO_2$ content in the exhaled breath of a patient to determine the patient's $CO_2$ blood concentration level, a device for supplying a treating gas to the patient and a device for detection of apnea.

The invention further relates to a method of manufacturing a nasal cannula comprising: a hollow main body having opposed first and second ends with a first opening formed in the first end and a second opening formed in the second end, and the main body defining an internal chamber therein; a partition dividing the internal chamber into first and second flow compartments, the first flow compartment communicating with the first opening and the second flow compartment communicating with the second opening; a flow passageway of a first nasal prong communicating with the first compartment and a flow passageway of the first mouthpiece communicating with the first compartment to define a first flow path communicating with both a first nostril and a mouth of the patient; and a flow passageway of a second nasal prong communicating with the second compartment and a flow passageway of the second mouthpiece communicating with the first compartment to define a second flow path communicating with both a second nostril and the mouth of the patient, the method comprising the steps of: assembling a main body mandrel with a pair of nasal mandrels and a pair of oral mandrels; dipping the mandrel assembly in a plastisol to form the nasal cannula on the mandrel assembly; and removing the main body mandrel, the pair of nasal mandrels and the pair of oral mandrels to thereby result in the nasal cannula.

BRIEF DESCRIPTION OF THE DRAWINGS

The invention will now be described, by way of example, with reference to the accompanying drawings, in which:

FIG. 5 is a fragmentary side elevation of the main body mandrel of FIGS. 1 and 2 taken along section line 5-5 of FIG. 2;

FIG. 6 is an elevation of the main body mandrel taken in the direction of arrow 6 in FIG. 5;

FIG. 13 a front elevational view of a further embodiment showing a partially assembled mandrel assembly having the pair of mouthpiece mandrels assembled with the pair of sections of the main body mandrel;

FIG. 13A a front elevational view of only the pair of sections of the main body mandrel;

FIG. 13B is a diagrammatic orthogonal view of a cannula, manufactured from the mandrel assembly of FIG. 13A, having a pair of separate mouthpieces and two separate flow passageways;

FIGS. 17A, 17B, 17C and 17D, respectively, are an isometric side view, opposing isometric end views and a side view of a nare manufacturing jig;

DETAILED DESCRIPTION OF THE EMBODIMENTS

Figure 1:
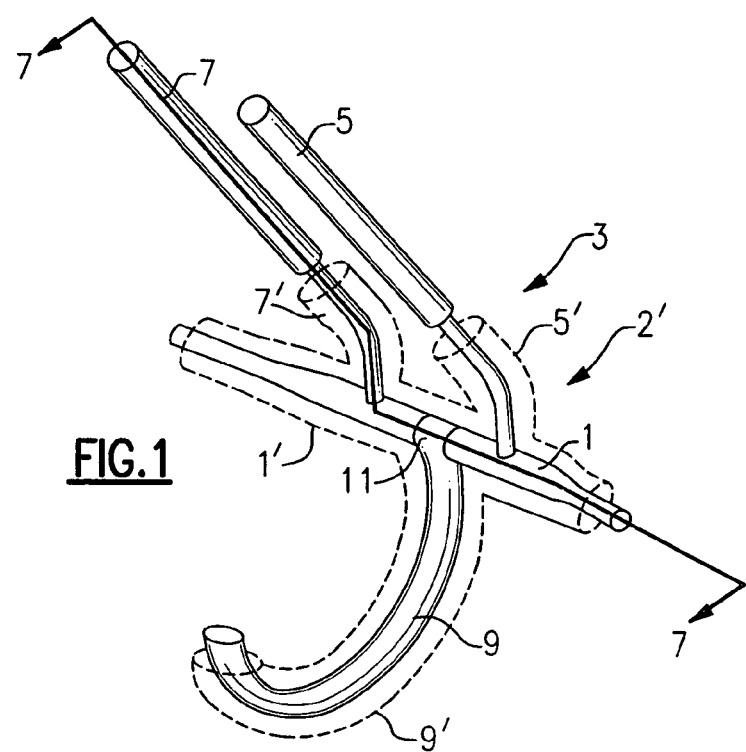
FIG. 1 is an orthogonal view of a cannula mandrel assembly with cannula forming plastics or polymeric material shown in ghost.

Referring to FIG. 1, the main body forming mandrel 1 of a beryllium copper cannula mandrel assembly 3 is shown with a pair of spaced apart nare forming mandrels 5 and 7, and a separate mouthpiece forming mandrel 9 having an end connector 11 for joining the mouthpiece mandrel 9 to the main body forming mandrel 1. A cannula 2', to be formed on the assembly, is shown in ghost and such cannula generally comprises a main body 1', a pair of nares 5', 7' and a mouthpiece 9' composed of polyvinyl chloride (PVC), for example.

Figure 2:
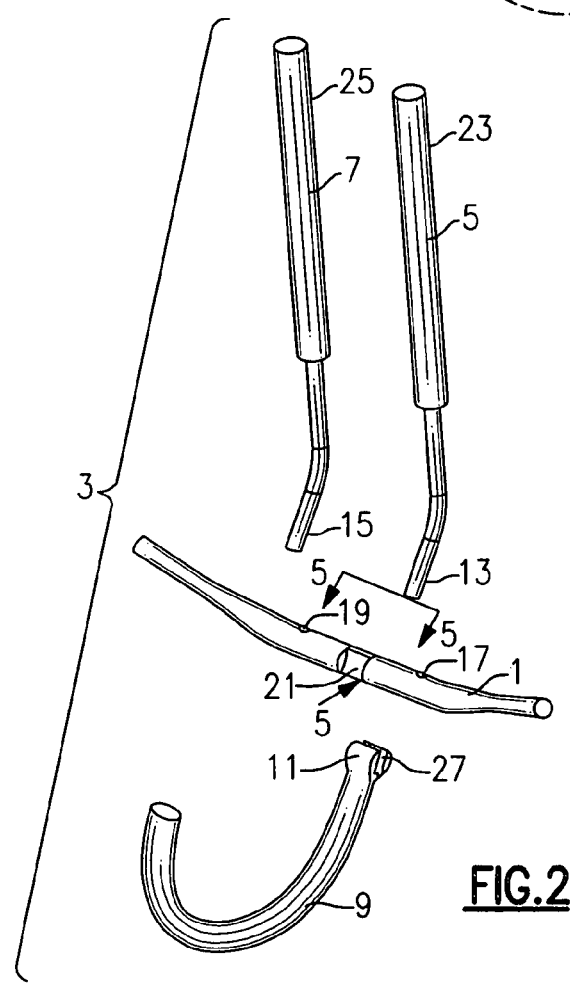
FIG. 2 is an orthogonal view of the cannula mandrel parts prior to assembly.

FIG. 2 shows the mandrel assembly components prior to assembly in order to form or produce the cannula mandrel assembly 3. Each of the nare mandrels 5 and 7 has a reduced diameter section 13 or 15 which form nares 5', 7', respectively, over which cannula forming plastics or polymeric material is applied. Reduced diameter sections 13 and 15 of nare mandrels 5 and 7 matingly slide into and are received by respective blind holes 17 and 19 of main body mandrel 1 (see FIG. 5). Main body mandrel 1 also has a central rectangular recessed section 21 which slidably mates and receives the end connector 11 of mouthpiece mandrel 9.

Nare mandrels 5 and 7 also have enlarged diameter sections 23 and 25 which facilitate support a plurality of identical cannula mandrel assemblies 3 in a jig (not shown) during the molding process. Additionally, the enlarged diameter enables sections 23 and 25 provide a larger contact surface which allows easier gripping of nare mandrels 5 and 7 to facilitate removal of the nare mandrels 5 and 7 from main body mandrel 1 after partial curing of the PVC, or some other plastisol or plastics material, on the cannula mandrel assembly 3.

FIG. 2 further shows the mouthpiece mandrel 9 with the end connector 11 which has a centrally located slot 27 (see FIG. 3) which slidably engages with the rectangular section 21 of the main body mandrel 1. Slot 27 is sized to permit close contact or engagement of the slot 27 with the rectangular section 21 of main body mandrel 1 such that a snug fit or attachment is obtained so as to removably retain the mouthpiece mandrel 9 on the main body mandrel 1 while also facilitating extraction of the mouthpiece mandrel 9 from the rectangular section 21 following partial curing of the PVC, or some other plastisol or plastics material, on the cannula mandrel assembly 3. The outer surface of end connector 11 is sized to approximate a continuation of the outer surface or diameter of main body mandrel 1 to provide a substantially uniform amount of applied PVC, or some other plastisol or plastics material, to the cannula mandrel assembly 3 and still facilitate withdrawal of the mouthpiece mandrel 9 from the cannula mandrel assembly 3 and the mouthpiece 9' of the cannula.

Figure 3:
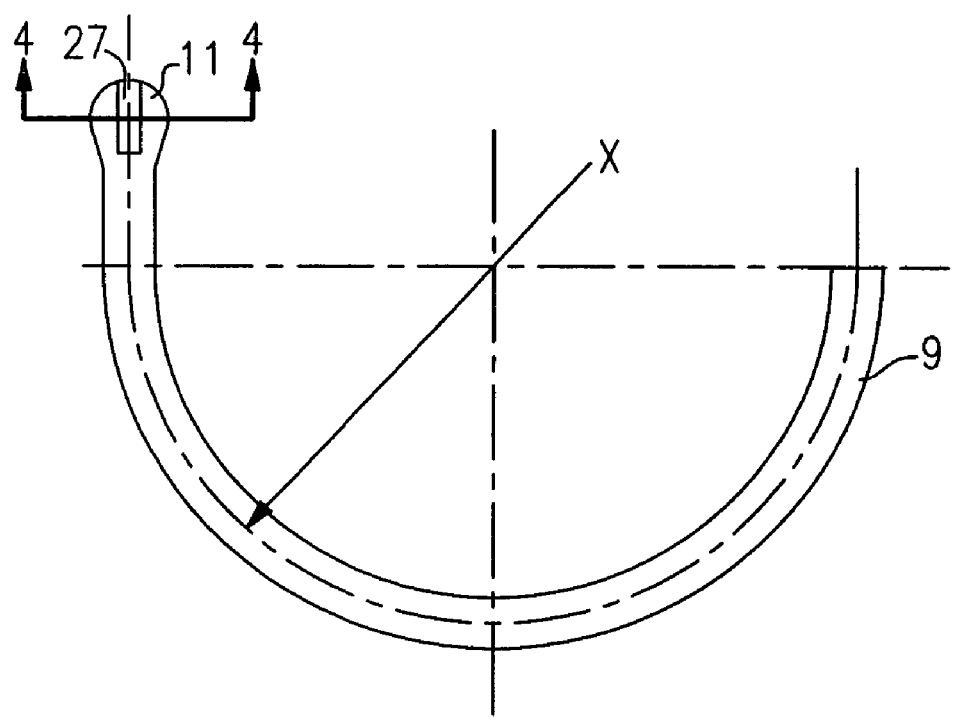
FIG. 3 is a side elevation of the mouthpiece mandrel of FIGS. 1 and 2 showing an end connector.

FIG. 3 shows the general contour of the mouthpiece mandrel 9 having a desired radius X with the end connector 11 located at one end of the mouthpiece mandrel 9 and having a slot 27 formed in the end connector 11.

Figure 4:
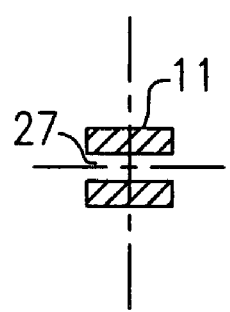
FIG. 4 is an end section of the end connector taken along section line 4-4 of FIG. 3.

FIG. 4 is a view along section line 4-4 of FIG. 3 which shows the shape, e.g., the length, the width, and the thickness, of the end connector 11 and the slot 27.

Referring to FIGS. 5 and 6, a pair of spaced apart blind holes 17 and 19 are formed in a central region of the main body mandrel 1. Each blind hole 17 and 19 is sized to matingly receive, via a sliding fit, one of the reduced diameter sections 13 or 15 of the nare mandrels 5 and 7 in order to engage and support nare mandrels 5 and 7 in a proper molding orientation during application of the PVC, or some other plastisol or plastics material, to the cannula mandrel assembly 3 for formation of the cannula 2'. The rectangular section 21 is made with a shoulder depth T removed to allow the diameter of end connector 11 of mouthpiece mandrel 9 to mate approximately flush with the diameter Y of main body 1.

The rectangular section 21 is shown preferably with a relieving radii R at opposed ends of the section. The relief radius R may be omitted if the main body mandrel 1 is machined or formed in a manner that allows this. Thickness Z of rectangular section 21 permits slot 27 of end connector 11 of mouthpiece mandrel 9 to firmly but slidably mate with rectangular section 21 and adequately maintain the engagement between those two components with one another during dipping. Width W of rectangular section 21 is just sufficient to closely accommodate end connector 11 of mouthpiece mandrel 9, e.g., a very small clearance fit between those two components is provided.

FIGS. 1 and 2 show nare mandrels 5 and 7 with bend sections 12 and 14. These bend sections 12 and 14 sufficiently curve or direct the nares of the cannula 2', following manufacture of the cannula, so that the nares may be properly aligned to be received within a patient's nasal cavities.

Although beryllium copper is the preferred material for manufacture of the cannula mandrel assembly 3, other materials which possess appropriate working temperature ranges, retain dimensional stability for reuse in a manufacturing environment and will easily and readily release the cannula 2' following partial curing of the PVC, or some other plastisol or plastics material, may be used. Metals including, but not limited to, steel, aluminum, bronze, brass, and copper alloys may be used, as well as some plastics materials. Beryllium copper is preferred due to its ability to transfer heat rapidly and reliably release the cured PVC, plastisol or other plastics material formed on the cannula mandrel assembly 3. Rapid heat transfer is desirable for the material forming the mandrel assembly both during heating of the cannula mandrel assembly 3 and following application of the cannula forming plastics or polymeric material where a partial cure of the plastics or polymeric material is followed by rapid cooling.

Prior to application of a plastics or polymeric solution, such as PVC, the cannula mandrel 3 is coated, usually by dipping step or process, with a silicone release layer or agent to facilitate separation and/or removal of the mandrel components from the plastics or polymeric material to be applied. The application of the plastics or polymeric material, in the preferred embodiment, is by dipping the silicone coated cannula mandrel assembly 3 which has been heated in an oven at an oven temperature of from about 350° F. to about 550° F. (preferably about 450° F.) for about 1 to about 3 minutes prior to dipping in a plastisol solution of PVC. One or more dipping steps may be performed to achieve the desired finished cannula material thickness and each of these dipping steps may be for a duration of 10-30 seconds, for example. During dipping, the mandrel is supported by the outer free enlarged sections 23 and 25 of the nare mandrels.

The use of a plastisol solution, such as PVC, provides a semi-clear finished cannula with sufficient strength to withstand subsequent attachment of various connectors while still being sufficiently flexibility to prevent injury or irritations to the user. Alternatively, other plastics or polymeric materials, which have material properties suitable for this method, capable of forming a plastisol, may be substituted for PVC.

Partial curing of the cannula takes place on the mandrel assembly 3. The cannula mandrel assembly with the partially cured PVC thereon is then placed in an oven, for a sufficient time, for further curing at a temperature from about 410° F. to about 450° F. Following curing to stabilize the PVC and after the cannula has sufficiently cooled, the mandrel components are then removed from the manufactured cannula and the release layer or agent assists with such removal, without damaging the cannula. The resulting manufactured nasal cannula has sufficient physical strength and retains its manufactured configuration.

Using the inventive method, a cannula with two nares and a mouthpiece is formed as follows: a cannula mandrel assembly 3 is formed by first, slidably mating reduced diameter sections 13 and 15 of nare mandrels 5 and 7 into the blind holes 17 and 19, respectively, of the main body mandrel 1; second, orienting nare mandrels 5 and 7 so that they are properly aligned as shown in FIG. 1; third, slidably mating the slot 27 of the end connector 11 of the mouthpiece mandrel 9 with the rectangular section 21 of the main body mandrel 1 in a desired orientation relative to the nare mandrels 5 and 7 so that it is also properly aligned as shown in FIG. 1; fourth, supporting the mandrel assembly in a jig and providing a silicone release layer or agent substantially encompassing the mandrel components; fifth, heating the assembled cannula mandrel assembly in an oven at a temperature of from about 350° F. to about 550° F.; sixth, providing a liquid uncured plastisol solution (PVC); seventh, dipping the cannula mandrel assembly into the liquid uncured plastisol solution (PVC), at least once, until the desired material thickness is built-up and/or achieved on the mandrel assembly 3; eighth, at least partially curing the plastisol (PVC) at a temperature of about 410° F. to about 450° F.; and ninth, following sufficient curing, removing the nare mandrels 5 and 7 from the blind holes 17 and 19 of main body mandrel 1 and the nares 5', 7' by pulling on enlarged diameter sections of the nare mandrels 5 and 7, and removing the mouthpiece mandrel 9 from the mouthpiece 9' by disengaging the slot 27 of the end connector 11 from the rectangular section 21 of the main body mandrel 1 and pulling the mouthpiece mandrel 9 out through the mouthpiece 9'; and finally slidably removing main body mandrel 1 from the main body 1' of the cannula by extracting or withdrawing the same from one end of the manufactured cannula 2'.

Figure 7:
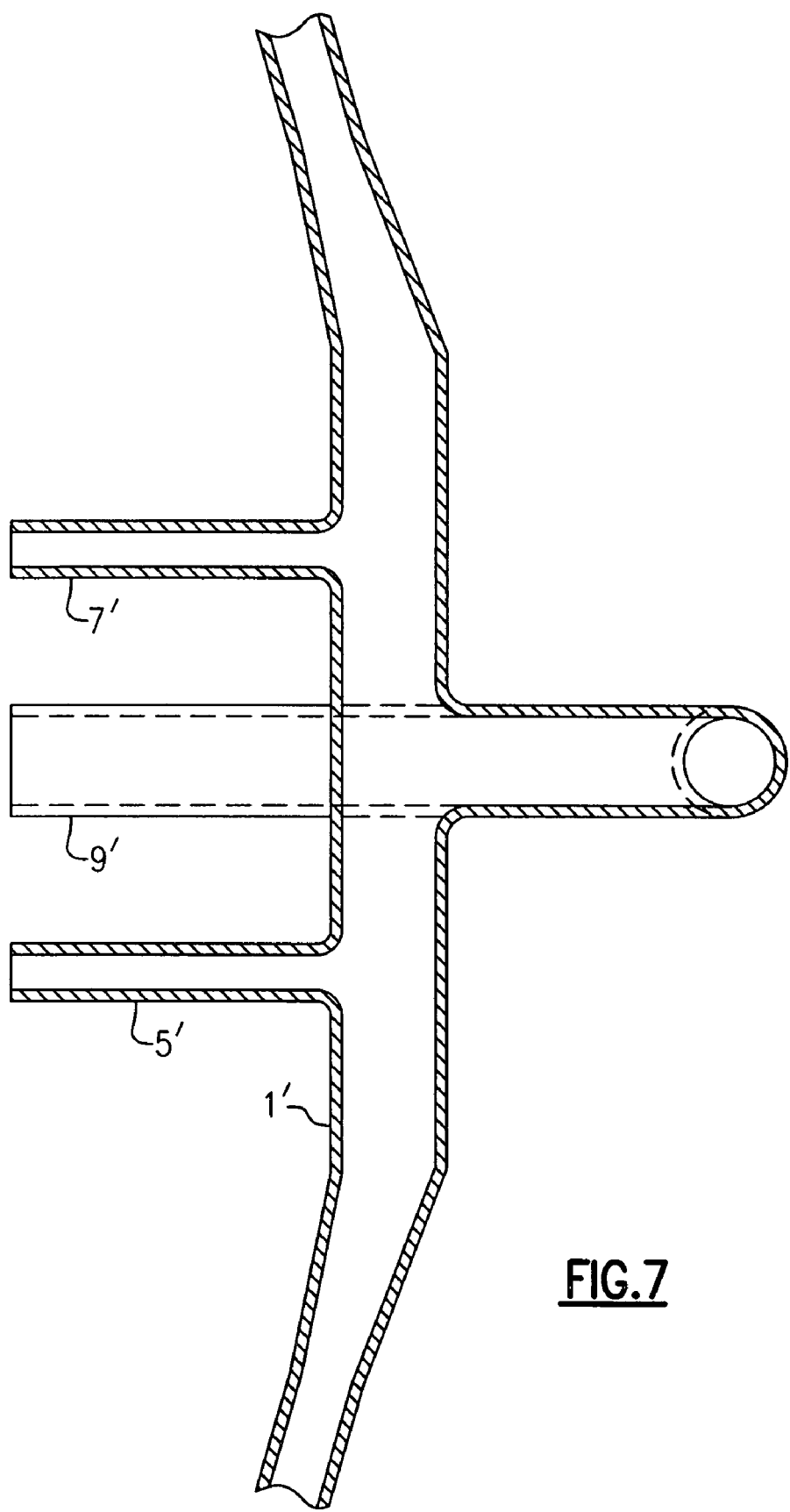
FIG. 7 is a diagrammatic cross-sectional view of a cannula, made by the method of the present invention, taken along section line 7-7 of FIG. 1.
Figure 8:
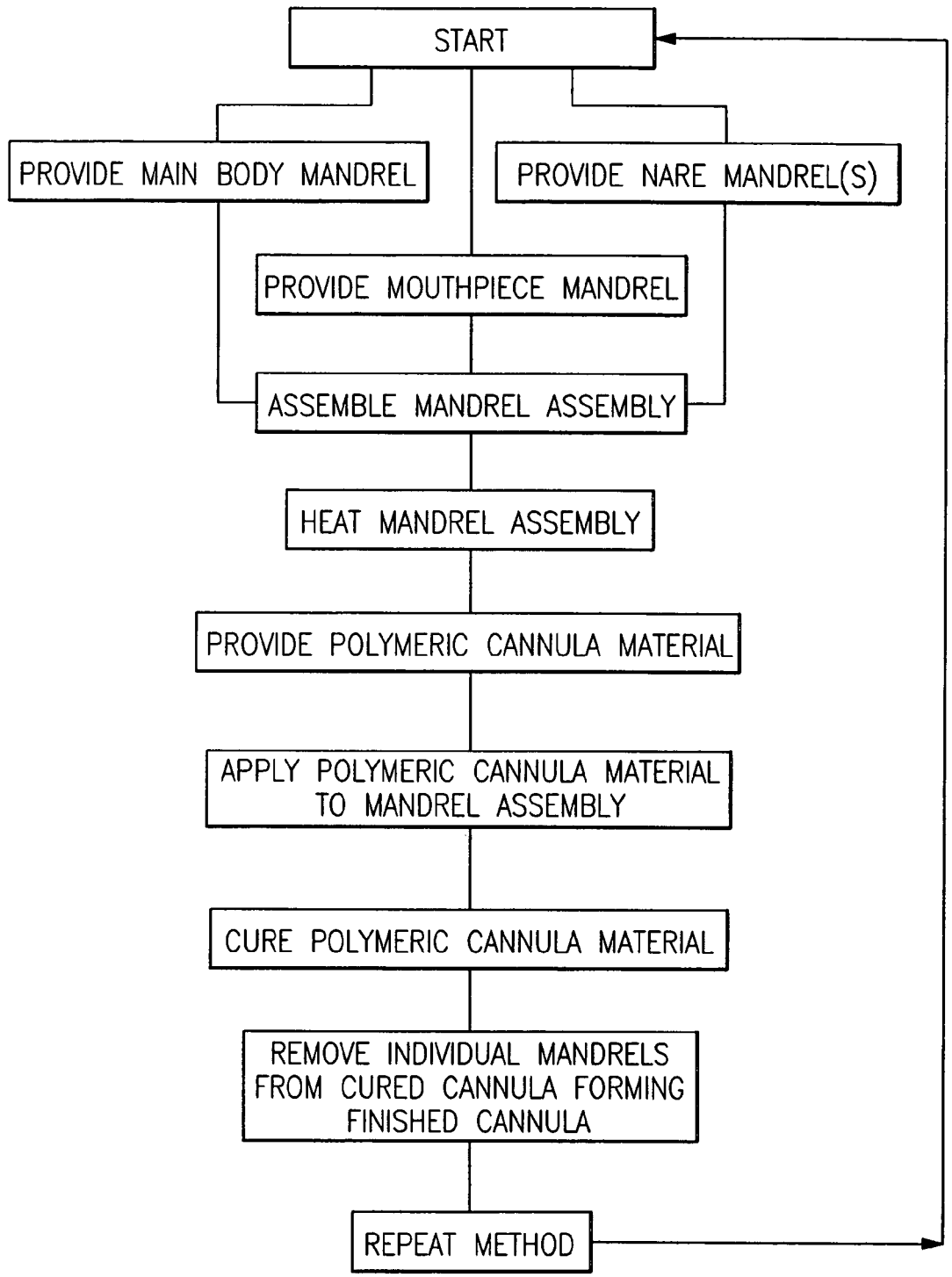
FIG. 8 is a flow diagram of the method of the present invention.

FIG. 7 shows a diagrammatic cross sectional view of a finished or manufactured cannula 2', following removal of the components of the cannula mandrel assembly 3 from the cured PVC cannula, and the formed contiguous flow paths through the main body 1', the nares 5' and 7' and the mouthpiece 9' can be seen.

It will be appreciated that the curing step may be completed in two stages, namely, a first partial cure of the PVC produced by the heated cannula mandrel assembly 3 which is sufficient to maintain the PVC on this assembly and a second stage in an oven at the above indicated curing temperatures to complete curing, following the partial curing of the PVC, the plastisol or some other plastics material.

It will be further appreciated that the opposed outer ends of the main body 1' of the manufactured cannula 2' may be trimmed, as necessary or desired, to provide a discrete area where a flexible connecting tubing or conduit may be connected thereto, e.g., by solvent bonding with MEK (methyl ethyl ketone) for example, and the mouthpiece 9' may be trimmed to a desired length suited to an individual patient so as to maximize the sensitivity of the finished cannula, e.g., sensing patient breathing, monitoring end tidal $CO_2$ in a patient's blood stream or supplying a treating gas to the patient.

It will also be understood that disassembly of the cannula mandrel assembly 3, following curing of the cannula forming polymeric material, can proceed by removing the mouthpiece mandrel before the nare mandrels as an obvious alternative method step, prior to removal of the main body mandrel.

One modification of the present invention relates to the addition or formation of an internal wall or septum in the internal passage of the cannula 2' to provide an internal partition or barrier therein, e.g., form a "divided cannula." The septum 29 divides the internal chamber C of the main body 1' of the cannula 2' into two separate compartments or passageways C1 and C2 so that a first one of the nares 5' can be coupled to a treating gas, such an oxygen source (not shown), to facilitate the supply of supplemental oxygen to one of the nostrils of a patient while the other one of the nares 7' and the central mouthpiece 9' can be coupled to a monitoring device (not shown), such as a transducer, to facilitate monitoring of breathing of the patient or coupled to a demand oxygen conserving device (not shown) while the patient, at the same time, is still able to receive, either continuously or intermittently during the sensed breathing cycle, a supplemental supply of oxygen. Alternatively, one of the nares 5' can be connected to a capnograph, for example, to sample the exhaled breath of a patient and detect the end tidal $CO_2$ in the blood stream of a patient or sensing of patient breathing.

In order to manufacture the septum 29, the main body forming mandrel 1 is formed as first and second separate, slightly spaced apart mandrel components 30, 31 which remain spaced apart from one another by a small gap or void 32 following assembly of the cannula mandrel assembly 3 and during the dipping operation of the manufacturing process so that the void 32 between the first and the second separate, slightly spaced apart mandrel components 30, 31 becomes filled with PVC, or some other plastisol or plastics material, and forms the septum 29. Once the cannula is adequately cured, the septum 29 forms an internal partition or barrier within the main body 1' of the cannula which divides the internal chamber C into two separate compartments or passageways C1 and C2.

Following sufficient curing, the nare mandrels 5 and 7 are removed from the blind holes 17 and 19 of main body mandrel 1 and the nares 5', 7' by pulling on enlarged diameter sections of nare mandrels 5 and 7, the mouthpiece mandrel 9 is removed from the mouthpiece 9' by disengaging the slot 27 of the end connector 11 from the rectangular section 21 of the main body mandrel 1 and pulling the mouthpiece mandrel 9 out through the mouthpiece 9'; and the first and second spaced apart components 30, 31 of the main body mandrel 1 are removed from the main body 1' of the cannula by pulling the first and second spaced apart components 30, 31 axially away from one another and out from the main body 1' of the cannula 2'. As discussed above, the opposed outer ends of the main body 1' of the manufactured cannula 2' may be trimmed, as necessary or desired, to facilitate connection to a connecting tubing or conduit.

This variation of the manufacturing process is suitable for intermittent nocturnal oxygen delivery even though the patient breaths through his or her mouth.

As can be seen in FIGS. 10A-10D and 11, another embodiment of the present invention relates to the cannula mandrel assembly 3 for forming a divided cannula having a pair of spaced apart mouthpieces. For the sake of clarity, the nare mandrels 5 and 7 are not shown attached respectively to the first or the second sections 1A, 1B of the main body forming mandrel 1. The first mouthpiece mandrel 49 comprises a first prong 53 for forming a first gas passageway 77 in the first mouthpiece of the manufactured cannula 60 and the second mouthpiece mandrel 49' comprises a second prong 53' for forming a second gas passageway 79 in the second mouthpiece of the manufactured cannula 60. A further description of the same follows below.

In order to attach both the first and second mouthpiece mandrels 49, 49' to the main body mandrel 1, each of the first and second mouthpiece mandrels 49, 49' include an end connector 51 (see FIG. 10C) attached to a connecting end 59 of the respective first and second prongs 53, 53'. The end connector 51 has a centrally located slot 57 which slidably engages or receives one of the two rectangular sections 21A, 21B (see FIG. 10B) formed in one of the two spaced apart but adjacent body sections 1A, 1B forming the main body mandrel 1, as described above. Each slot 57 is sized to closely contact and engage the respective rectangular section 21A or 21B of main body mandrel 1 of each body section 1A, 1B such that a snug fit and retention of each respective mouthpiece mandrel 49, 49' with the main body mandrel 1 is obtained both prior to and during dipping while still also facilitating extraction of the mouthpiece mandrels 49, 49' from rectangular sections 21A, 21B following partial curing and cooling of the PVC, or some other plastisol or plastics material. As with the other embodiments, the outer surface of end connector 51 has a shape, a size and/or contour which approximates the outer diameter of the main body mandrel 1 to provide a uniform diameter of applied cannula forming polymeric material while also facilitating withdrawal of the mouthpiece mandrels 49, 49' from the mouthpieces 69, 69' of the manufactured cannula 60 (see FIG. 11).

The first and second mouthpiece mandrels 49, 49' once coupled to the main body mandrel 1, extend parallel to but are spaced from one another by a small distance, e.g., 1/16 to 1/2 inch or so, more preferably spaced from one another by a distance of 1/4 of an inch. The first and second prongs 53, 53' each have a cross sectional area of between about 0.006 and about 0.007 square inches and a radius of curvature R1 of between about 0.5 of an inch to about 2.5 inches or so, and more preferably a radius of curvature of between about 0.75 of an inch to about 1.25 inches or so. The radius of curvature R1 can vary but is generally chosen to facilitate the alignment of the cannula mouthpiece with a patient's open mouth. The separation between the first and second prongs 53, 53', according to this embodiment, forms a uniform elongate spacing or area between those to prongs so that a sufficient space is provided during the dipping operation(s), which applies a plastisol coating to the cannula mandrel assembly 3 and each of the first and second prongs 53, 53' without any plastisol interconnecting or joining the two mouthpieces 69, 69' with one another, i.e., the two mouthpieces 69, 69' are completely separate and movable independent of one another following formation of the cannula 60.

The transverse cross sectional area D (see FIG. 11) of the openings 83, 87 and the internal gas flow passageway 77, 79 within the mouthpiece 69, 69' of the cannula, once the first and second prongs 53, 53' are removed therefrom, are sufficiently sized for supplying a desired treating gas to a patient, for example, via a demand regulator to a mouth breathing patient. Alternatively, the respective internal gas flow passageway within the mouthpiece 69, 69' of the cannula is sufficiently sized to allow withdrawal, detection, sampling, etc., of an exhalation gas(es) from a mouth of a breathing patient. It is to be appreciated that the transverse cross sectional area of the internal gas flow passageway, formed in the mouthpiece 69, 69' for supplying a treating gas to a patient, may typically be larger than the transverse cross sectional area of a gas flow passageway for withdrawing or sampling a gas(es) from a patient. But, for the sake of simplicity of manufacture and for added versatility, the transverse cross sectional areas of both formed internal gas flow passageways 77, 79 in the first and second mouthpieces 69, 69' can be manufacture identical to one another.

Figure 11:
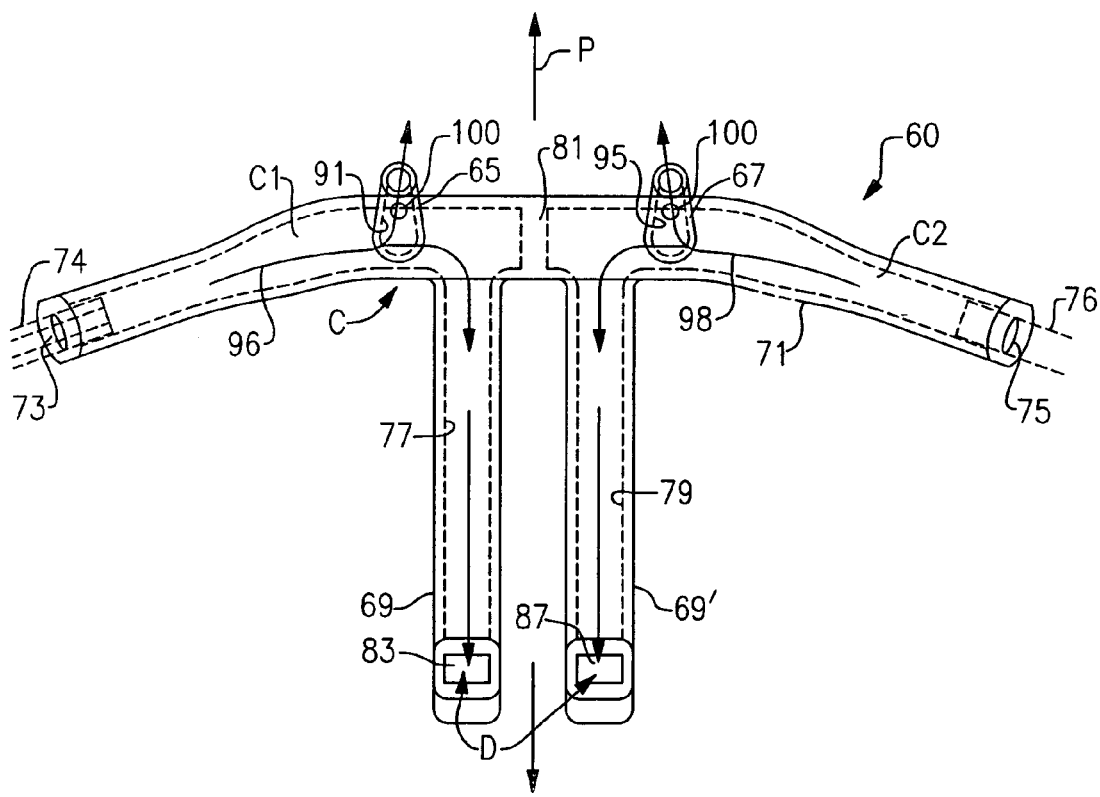
FIG. 11 is a diagrammatic orthogonal view of a cannula, manufactured from the mandrel assembly of FIG. 10, having a pair of separate mouthpieces and two separate flow passageways.
Figure 10B:
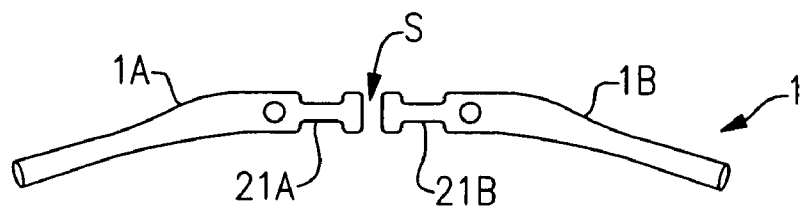
FIG. 10B a front elevational view of only the pair of sections of the main body mandrel.
Figure 10A:
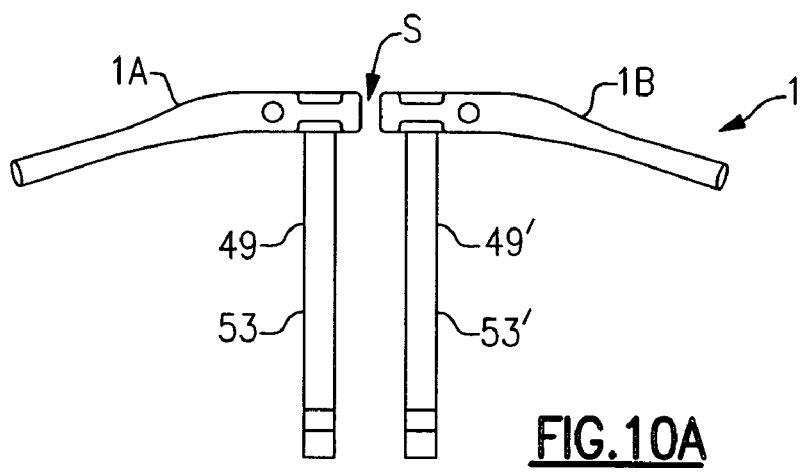
FIG. 10A a front elevational view of another embodiment showing a partially assembled mandrel assembly having the pair of mouthpiece mandrels assembled with the pair of sections of the main body mandrel.
Figure 10C:
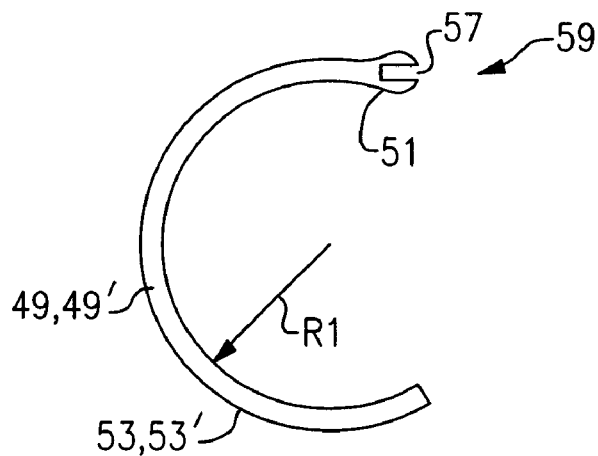
FIG. 10C a side elevational view of one prong for forming the gas flow passageway in the mouthpiece.
Figure 10D:
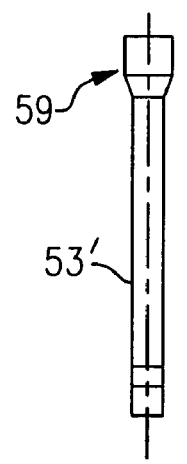
FIG. 10D a front elevational view of the prong of FIG. 10C.

The above described first and second mouthpiece mandrels 49, 49' are each assembled with one of the body sections 1A or 1B of the main body mandrel 1 and one of the first and second nare mandrels 5, 7 to form the cannula mandrel assembly 3. Before dipping, the cannula mandrel assembly 3 is sprayed or otherwise coated with an release film, layer or agent and pre-heated to a desired temperature and then dipped in the cannula forming polymeric plastisol to provide a desired thickness or layer of a partially cured plastics or polymeric material on the exterior surface of the cannula mandrel assembly 3 and thereby form a manufactured plastisol cannula. The partially cured manufactured plastisol cannula is again heated in an oven to further cure the plastics or polymeric material, as previously described. After sufficient curing of the plastics or polymeric material, both of the first and second nare forming mandrels 5, 7, the first and second mouthpiece forming mandrels 49, 49' and the first and second sections 1A, 1B of the main body forming mandrels 1 are extracted from the cured polymeric material and the remaining cured structure results in the manufactured and cured cannula 60, as shown in FIG. 11. If desired or necessary the end of the cannula 60 can be trimmed to a desired length.

The manufactured cannula 60, formed from the above described process and cannula mandrel assembly 3 shown in FIGS. 10A-10D, after addition of the nare mandrels 5 and 7, comprises a main body 71 with a pair of opposed internal chamber end openings 73, 75 located at opposite ends of the main body 71 for coupling, by an adhesive such as MEK for example, each opposed end of the cannula to a flexible gas delivery, pressure detecting or gas sampling tubing or some other conduit 74, 76 (only partially shown in FIG. 11). The gap or spacing formed between the adjacent ends of the first and second sections 1A, 1B of the main body forming mandrel 1 (see FIGS. 10A and 10B) creates a partition, a wall, a dividing member or a septum 81 which divides the internal chamber C into a first compartment or passageway C1 and a completely separate second compartment or passageway C2. The first compartment or passageway C1 communicates with the first chamber end opening 73 while the second separate compartment or passageway C2 communicates with the second chamber end opening 75. A first fluid passageway 91, formed in the first centrally located nasal prong 65, communicates with the first compartment or passageway C1 while a second fluid passageway 95, formed in a second centrally located nasal prong 67, communicates with the second separate compartment or passageway C2. The first gas passageway 77, formed in the first mouthpiece 69, communicates with the first compartment or passageway C1 while the second gas flow passageway 79, formed in the second mouthpiece 69', communicates with the second separate compartment or passageway C2. The pair of centrally located but spaced apart nasal prongs 65, 67 are formed on the cannula for insertion into the nostrils of a patient's nose while the first and second centrally located mouthpieces 69, 69' are formed in the cannula substantially adjacent the middle section of the main body 71, between the nasal prongs 65, 67, for communication with the mouth of the patient.

Figure 11A:
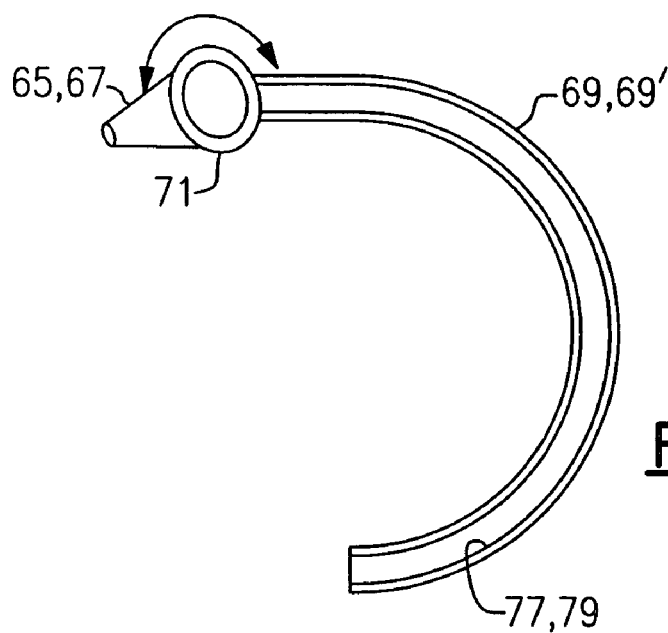
FIG. 11A is a diagrammatic side elevational view of a cannula of FIG. 11.

As best seen in FIG. 11A, the first and second mouthpieces 69, 69' of the nasal cannula 60 are shown in their originally molded shape or configuration which generally corresponds to the curvature of the mouthpiece mandrel 49. As can be appreciated, due to the nature of the resiliency of the plastisol material which forms the cannula 60, the first and second mouthpieces 69, 69' will generally retain and/or return back to such originally molded curvature. As discussed above, the mouthpiece 69, 69' may be trimmed to a desired length (shown in dashed lines in FIG. 12B) to suited an individual patient so as to maximize the sensitivity of the cannula, e.g., sensing patient breathing, monitoring end tidal $CO_2$ in a patient's blood stream, supplying a treating gas to the patient, detecting sleep apnea, etc. That is, the gas passage openings 83 and 87 are generally aligned with, e.g., extends substantially perpendicular to, the exhalation/inhalation path E of the patient.

It is to be appreciated that the nasal cannula 60 is a unitary structure comprising two completely separate internal flow paths 96 and 98. Each one of the two completely separate internal flow paths 96 and 98 is suitable for supplying a treating gas to a patient both via a nostril and the mouth of a patient as well as capable of withdrawing or sampling an exhalation gas(es) from the patient, or monitoring breathing characteristics, detecting pressure, etc. The first compartment or passageway C1, of the internal chamber C of the main body of the cannula 60, is in constant and continuous communication with the first gas passageway 77 of the first mouthpiece 69 and also in constant and continuous communication with the first gas passageway 91 in the first nasal prong 65 and all of these compartments and passageways form the first completely separate internal flow path 96. The second compartment or passageway C2, of the internal chamber C of the main body of the cannula 60, is in constant and continuous communication with the second gas passageway 79 of the second mouthpiece 69' and also in constant and continuous communication with the second gas passageway 95 in the second nasal prong 67 and all of these compartments and passageways form the second completely separate internal flow path 98. As a result of these completely separate fluid passageways 96, 98, each completely separate fluid passageway 96 or 98 can facilitate preforming one of the following functions: monitor breathing of a patient via the mouth and/or the nose, sampling the end tidal $CO_2$ content in the exhaled breath of a patient via the mouth and/or the nose to determine the patient's $CO_2$ concentration level in the blood, supplying a treating gas to a patient via the mouth and/or the nose, detecting apnea via the mouth and/or the nose, etc. If desired, the septum 81 may be eliminated so that the first and second compartments or passageways C1 and C2, the first and second internal gas passageways 77, 79 and the first and second gas passageways 91 and 95 in the nasal prongs 65 and 67 are all in constant and continuous communication with one another.

It is to be appreciated that it is not necessary to have the two mouthpieces 69, 69' precisely centered between the nasal prongs 65, 67. It is conceivable that the mouthpieces could be located on one side or the other of a central plane P bisecting a center of main body 71 into two halves. It is to be appreciated further that it is not necessary to have the septum 81 center within the main body as long as the septum 81 is generally located between the nasal prongs 65, 67. Also, as set forth in U.S. Pat. No. 6,439,234 to Curti et al., the disclosure of which is hereby incorporated by reference, additional openings 100 (shown as dashed lines in FIG. 11), preferably adjacent the remote free end of each nasal prong, could be provided in the nasal prongs 65, 67 and possibly in the gas passageway 69, 69' of the mouthpiece to prevent occlusion of the nasal prongs and facilitate monitoring, detecting, sampling, delivery, etc.

As can be seen in FIG. 11A for example, the first end of the nasal prongs 65 and 67 generally form an angle of between about 180° or so ±5 degrees with the connected end of the mouthpieces 69, 69'.

Figure 12A:
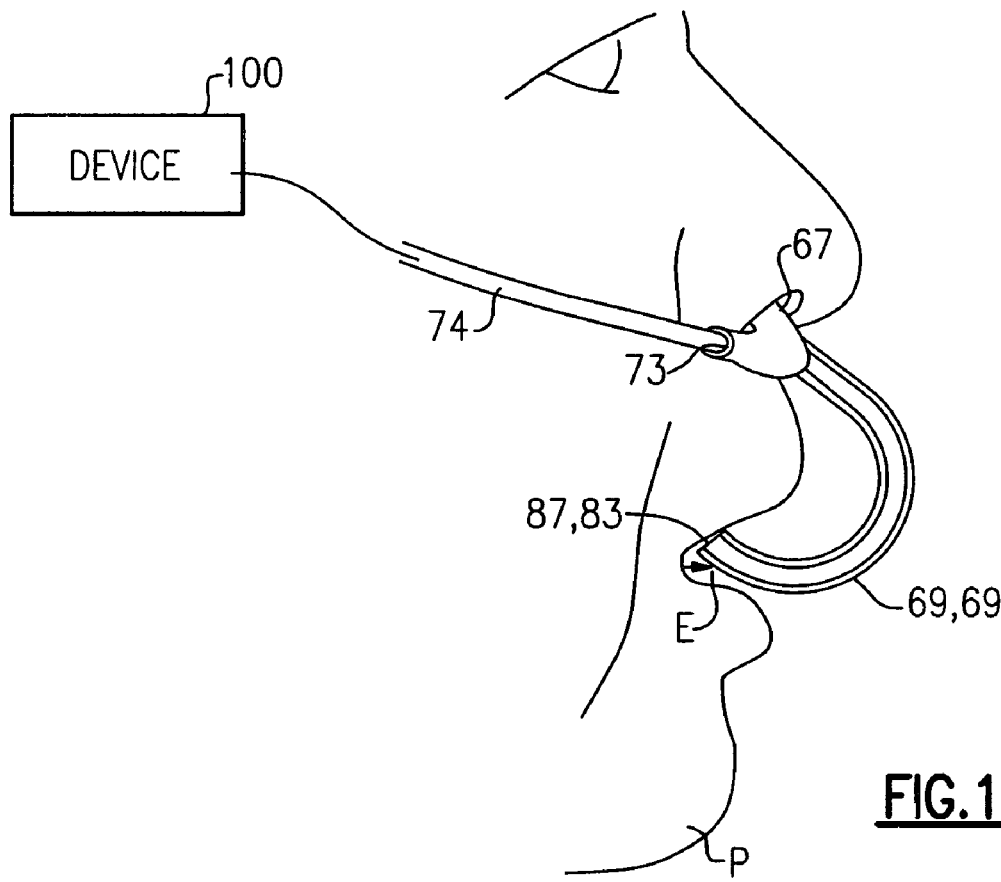
FIG. 12A is a side elevational views showing the originally molded orientation of the mouthpiece relative to an open mouth of a patient.
Figure 12B:
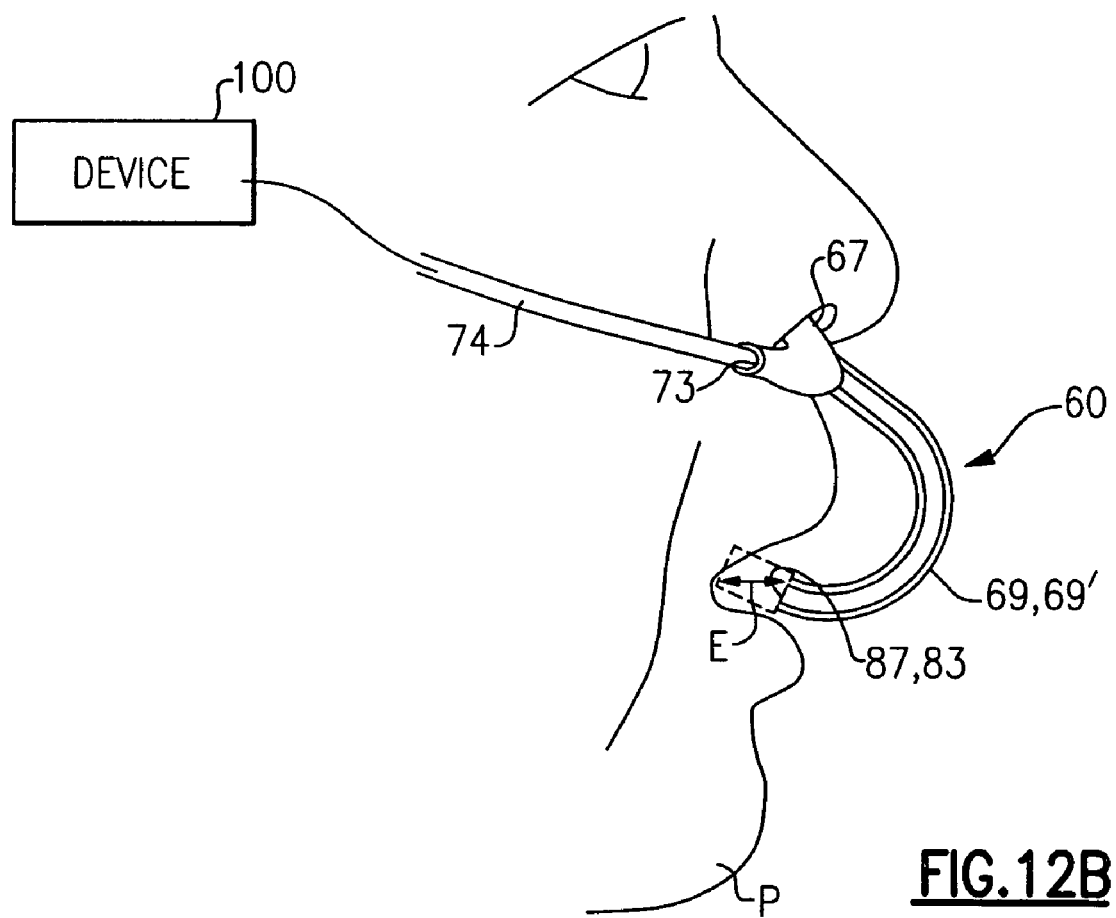
FIG. 12B is a side elevational view showing the trimmed orientation of the mouthpiece, relative to an open mouth of a patient, for aligning an opening of the mouthpiece with the patient's oral inhalation/exhalation path.

FIG. 12A shows a typical orientation of the mouthpieces 69, 69', relative to a patient's mouth in an opened position following installation of the cannula on the patient. As can be readily observed in FIG. 12A, it is possible that the gas passage openings 83 and 87 initially may not be precisely aligned with the exhalation/inhalation path E of the patient, e.g., the plane defined by the gas passage openings 83 and 87 may not extend substantially normal to the exhalation/inhalation path E. The remote free end of the mouthpieces 69, 69' can be cut or trimmed, as necessary (see FIG. 12B in which the removed or trimmed portion of the mouthpieces 69, 69' is shown in dashed lines), so that thereafter the openings to the internal gas passageways 77, 79 of the mouthpieces 69, 69' lies substantially normal to the exhalation/inhalation path E of the patient. Such alignment of the openings 83 and 87 to the internal gas passageways 77, 79 of the mouthpieces 69, 69' assists with better collection of a gas sample(s), more accurate detection of an exhalation pressure, more accurate delivery of a gas(es), more accurate monitoring of the patient's breathing, etc. The above described arrangement permits minor adjustment of the configuration and/or orientation of the mouthpieces 69, 69'.

With reference to FIGS. 13 and 13A, another embodiment of the cannula mandrel assembly will now be discussed. For the sake of clarity, the nare mandrels are not shown attached respectively to the first or the second sections 1A, 1B of the main body forming mandrel 1 in FIG. 13. As this embodiment is similar to the previous embodiments, identical reference numerals will given to identical elements and only the differences between this embodiment and the embodiment of FIGS. 10A-10D, in particular, will be discussed in detail.

The principal difference between this embodiment and the embodiment of FIGS. 10A-10D is that the rectangular sections 21A and 21B are located slightly closer to one another so the first and second prongs 53, 53', when engaged therewith, are mounted in a closer relationship to one another. That is, each rectangular section 21A and 21B is located about 0.0290 inches of so from an end of either the first or the second sections 1A, 1B of the main body forming mandrel 1 and so that adjacent edges of the first or the second sections 1A, 1B are spaced from one another by a distance of about 0.050 inches. This results in the first and second prongs 53, 53', when engaged with the respective rectangular sections 21A, 21B, being spaced or separated from one another by only a distance of about 0.1100 inches or so.

The net result of this modification occurs during the dipping process. That is, during the dipping process, the first and second prongs 53, 53' are located sufficiently closed to one another such that the plastisol at least partially fills the space or gap formed between the first and second prongs 53, 53' and forms an interconnecting web 89 and well as encases and surrounds each one of the first and second prongs 53, 53 to form an integral mouthpiece comprising a pair of joined or interconnected mouthpieces 69, 69' (see FIG. 13A) which move in unison with one another. In all other respect, this embodiment is substantially identical to the embodiment of FIGS. 10A-10D, 11 and 11A.

Figure 14:
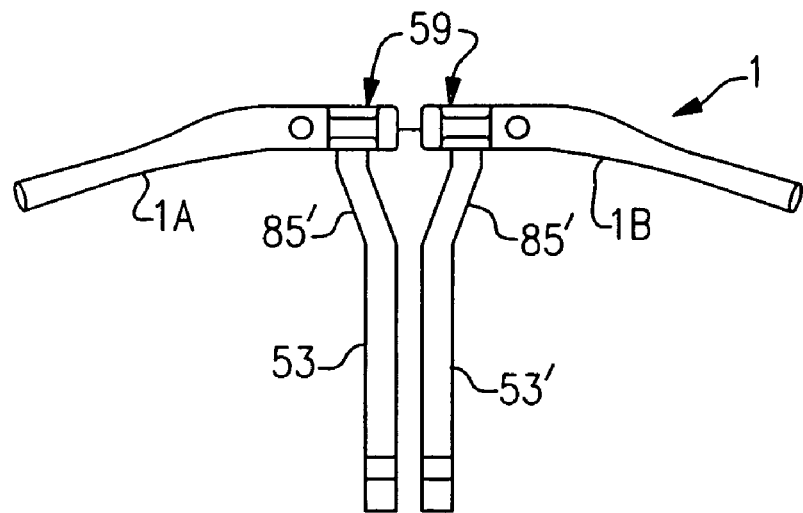
FIG. 14 a front elevational view of still another embodiment showing a partially assembled mandrel assembly having the pair of mouthpiece mandrels assembled with the pair of sections of the main body mandrel.
Figure 14A:
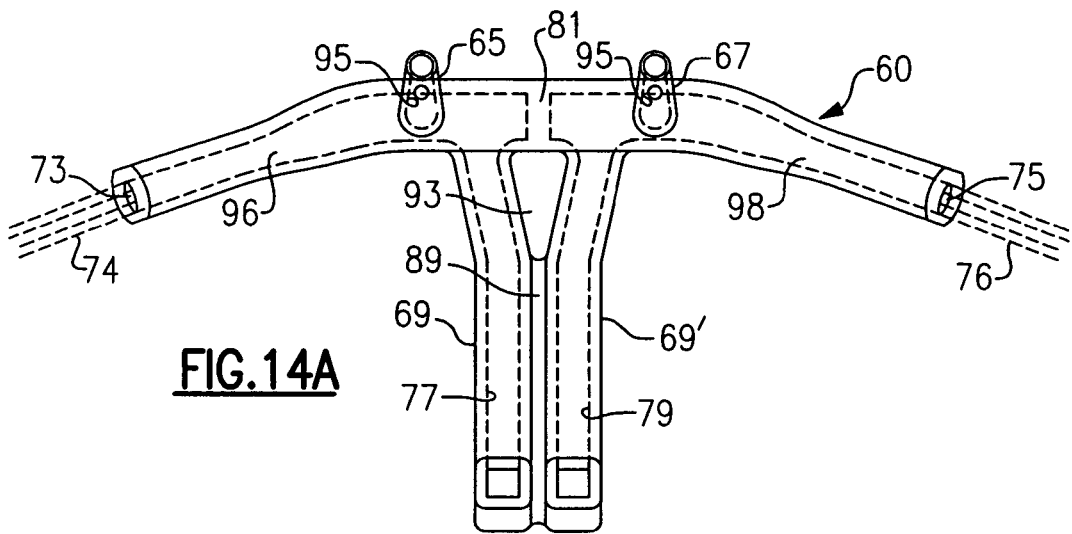
FIG. 14A is a diagrammatic orthogonal view of a cannula, manufactured from the mandrel assembly of FIG. 14, having a pair of separate mouthpieces and two separate flow passageways.

With reference to FIGS. 14 and 14A, another embodiment of the cannula mandrel assembly will now be discussed. For the sake of clarity, the nare mandrels are not shown attached respectively to the first or the second sections 1A, 1B of the main body forming mandrel 1 in FIG. 14. As this embodiment is similar to the previous embodiments, identical reference numerals will given to identical elements and only the differences between this embodiment and the embodiment of FIGS. 10A-10D, in particular, will be discussed in detail.

The principal difference between this embodiment and the embodiment of FIGS. 10A-10D is that each one of the first and second prongs 53, 53' has a small inwardly directed bend or transition 85 formed adjacent the connecting end 59 of the respective first and second prongs 53, 53'. As a result of this small inwardly directed bend or transition 85 toward one another, when the first and second prongs 53, 53' are engaged with the respective first and second sections 1A, 1B, the connecting ends 59 are located further away from one another while the remote free ends of the first and second prongs 53, 53' are located in a closer spaced relationship to one another. That is, the connecting ends 59 of the first and second prongs 53, 53' are spaced from one another by a distance of about 1/16 to 1/2 inch or while the remote free ends of the first and second prongs 53, 53' are spaced from one another by a distance of about 0.110 inches or so, similar to the embodiment of FIGS. 13 and 13A.

The net result of this modification occurs during the dipping process. That is, during the dipping process, the remote free ends of the first and second prongs 53, 53' are located sufficiently closed to one another such that the plastisol at least partially fills the space or gap between the first and second prongs 53, 53' to form a web 89 therebetween, as well as encases and surrounds each one of the first and second prongs 53, 53 to thereby result in an integral mouthpiece comprising a pair of joined or interconnected mouthpieces 69, 69', once the first and second prongs 53, 53 are removed, which move in unison with one another. In all other respect, this embodiment is substantially identical to the embodiment of FIGS. 10A-10D, 11 and 11A. A through hole 93, which does not contain any plastisol, is formed in the cannula 60 and spaces the web 89 from the main body 71.

Figure 15:
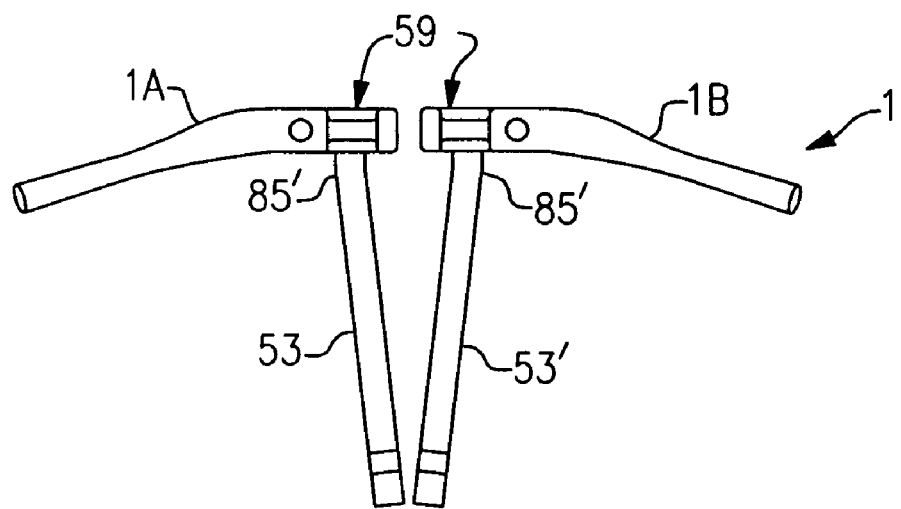
FIG. 15 a front view of yet another embodiment showing a partially assembled mandrel assembly having the pair of mouthpiece mandrels assembled with the pair of sections of the main body mandrel.
Figure 15A:
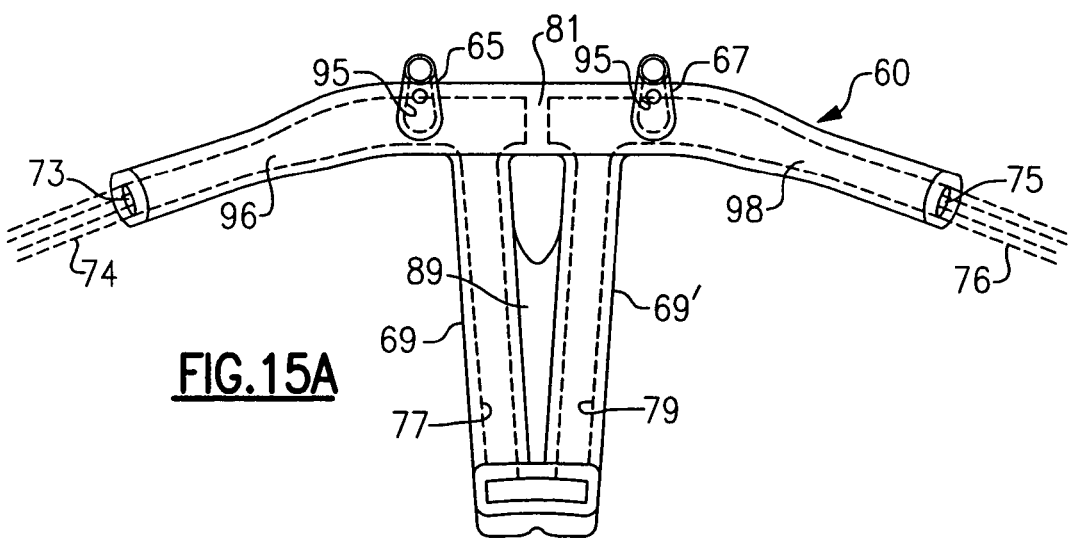
FIG. 15A is a diagrammatic orthogonal view of a cannula, manufactured from the mandrel assembly of FIG. 15, having a pair of separate mouthpieces and two separate flow passageways.

With reference to FIGS. 15 and 15A, a still further embodiment of the cannula mandrel assembly will now be discussed. For the sake of clarity, the nare mandrels are not shown attached respectively to the first or the second sections 1A, 1B of the main body forming mandrel 1 FIG. 15. As this embodiment is similar to the previous embodiments, identical reference numerals will given to identical elements and only the differences between this embodiment and the embodiment of FIGS. 10A-10D, in particular, will be discussed in detail.

The principal difference between this embodiment and the embodiment of FIGS. 10A-10D is that each one of the first and second prongs 53, 53' has a very gradual inclination or taper 85' toward one another, commencing adjacent the connecting end 59 of the respective first and second prongs 53, 53' and extending all the way to the free ends of the first and second prongs 53, 53'. As a result of very gradual inclination or taper toward one another, when the first and second prongs 53, 53' are engaged with the respective first and second sections 1A, 1B, the remote free ends of the first and second prongs 53, 53' are located in very close or possibly in abutting engagement or contact with one another. That is, the remote free ends of the first and second prongs 53, 53' are either in contact with one another or spaced from one another by a distance of less than 0.050 inches or so.

The net result of this modification occurs during the dipping process. That is, during the dipping process, the remote free ends of the first and second prongs 53, 53' are located sufficiently closed to one another such that the plastisol at least partially fills the space or gap between the first and second prongs 53, 53' to form a web 89 therebetween, as well as encases and surrounds each one of the first and second prongs 53, 53 to thereby result in an integral mouthpiece comprising a pair of joined or interconnected mouthpieces 69, 69' which, once the first and second prongs 53, 53 are removed, move in unison with one another. The opening for the two passageways 77, 79 is, in essence, a single common enlarged opening communicating with both passageways 77, 79. A through hole 93, which does not contain any plastisol, is formed in the cannula 60 and spaces the web 89 from the main body 71. In all other respect, this embodiment is substantially identical to the embodiment of FIGS. 10A-10D, 11 and 11A.

According to this application, the term "nasal cannula facepiece" generally comprises: (1) a hollow main body defining an internal chamber therein and having opposed first and second ends; and (2) at least one and preferably first and second nasal prongs which each communicate with the internal chamber of the main body and define respective first and second nasal prong passages.

It is to be appreciated that the mouthpiece could also be injection molded as a single unitary piece or injection molded as two separate pieces, i.e., the facepiece separately molded from the mouthpiece, which are subsequently assembled with one another. Alternatively, the cannula facepiece could also be either injection molded or formed with by polymeric material which is cured. The cannula mouthpiece could be formed by injection molding, by a polymeric material which is cured, or extruded as a separate piece. The facepiece and the mouthpiece are subsequently assembled with one another to form a manufactured cannula.

The cannula, manufactured according to the present invention, is primarily a divided cannula having two completely separate gas flow paths with each completely separate flow path communicating both with the nasal cavity, via one of the patient's nostrils, and the mouth or the oral cavity of the patient. Each one of the mouthpieces, for communicating with the mouth or the oral cavity of the patient, is molded with a sufficient curvature and of a sufficient length such that the free end of both mouthpieces will be typically located closely adjacent, or in direct contact with, the upper lip or lip region of the patient, depending upon the facial contour(s) of the patient. The curvatures of the mouthpieces in combination with the excess length of the mouthpieces results in extra mouthpiece material to facilitate trimming of an excess portion of the free thereof so that the openings, for both mouthpieces, can be aligned substantially normal to the inhalation/exhalation path of the patient and thereby increase the sensitivity of the cannula.

Considering still further embodiments of the present invention, it has been described herein above that the present invention is directed to a nasal cannula, and a method and apparatus for making a nasal cannula, wherein the nasal cannula provides a number of flow paths for providing treatment gas or gases to a patient and for monitoring the patient's respiration, including the breathing pattern and gases in the patient's breathing. For example, the nasal cannula illustrated, for example, with reference to FIG. 1, includes a main body having a single flow chamber an opening to the exterior at each end of the main body, two nasal prongs, each with a nasal flow passage connected fro the flow chamber, and a single mouthpiece with a mouthpiece flow passage connected from the main body flow chamber All of the interior passages of the nasal cannula of the type shown in FIG. 1 thereby form a single, common flow path with five "ports", the "ports" including two to the nostrils, one to the mouth and two to the exterior. Of these five "ports", therefore, two are dedicated to the nostrils and one to the mouth, leaving the two openings from the main flow chamber to the exterior available for, for example, connection to a source of treatment gas or to some form of monitoring or measurement device. It must be noted, however, that because all five ports are interconnected into a single flow path centered in the single main flow chamber, the ports are not separate and independent from one another.

The embodiments of the nasal cannula of the present invention illustrated, for example, with reference to FIGS. 10, 11, 13, 14 and 15, are thereby designed to provide additional separate and independent flow paths, thereby allowing additional and more flexible connections to sources of treatment gases and monitoring and measurement devices.

In these embodiments of a nasal cannula of the present invention, the nasal cannula again includes a hollow main body having an internal chamber and having opposed first and second ends with a first opening formed in the first end and a second opening formed in the second end. The internal chamber in the hollow main body includes, however, a partition dividing the internal chamber into first and second flow compartments wherein the first flow compartment communicates with the first opening and the second flow compartment communicates with the second opening.

The cannula again includes first and second nasal prongs and now includes first and second mouthpieces and the first and second nasal prongs respectively include a first nasal flow passageway and a second nasal flow passageway and the first and second mouthpieces respectively include a first mouthpiece flow passageway and a second mouthpiece flow passageway. In these embodiments, the first nasal flow passageway, the first mouthpiece flow passageway and the first opening into the first flow compartment in the main body are interconnected through the first flow compartment in the main body to form a first flow path communicating with and common to a first nostril, the mouth of the patient and the first opening in the main body. The second nasal flow passageway, the second mouthpiece flow passageway and the second opening in the main body are in turn interconnected through the second flow compartment in the main body to form a second flow path communicating with and common to a second nostril, the mouth of the patient and the second opening in the main body.

The embodiments of nasal cannula illustrated in FIGS. 10, 11, 13, 14 and 15 thereby each provide two separate and independent flow paths wherein each flow path is comprised of a flow compartment in the main body and the nasal flow passageway, mouthpiece passageway and opening branching off from the flow compartment. The gas sources or monitoring or measurement devices connected to one flow path are thereby separate and independent from the gas sources or monitoring or measurement devices connected to the second flow path, so that one does not effect the other except through the internal flow paths of the nostrils, mouth and throat of the patient. The embodiments shown in FIGS. 10, 11, 13, 14 and 14 thereby allowing additional and more flexible connections to sources of treatment gases and monitoring and measurement devices and reducing mutual interaction or interference between the gas sources and devices connected to the nasal cannula.

Figure 16A:
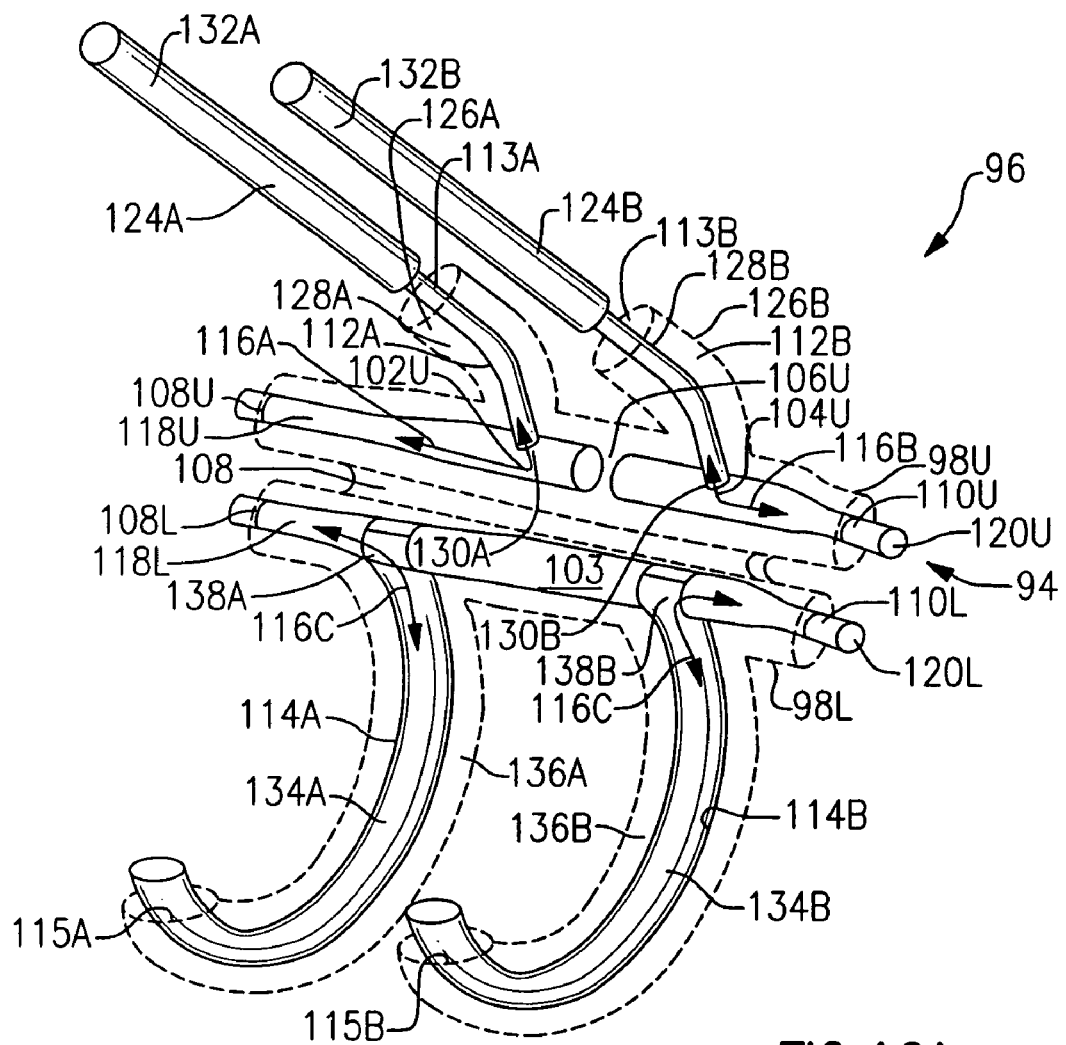
FIG. 16A is a diagrammatic orthogonal view of an alternate cannula assembly, with a manufacture cannula shown in dashed lines, in which the cannula has a pair of separate mouthpieces and a pair of separate nares with each of the mouthpieces and nares having the ability to provide the cannula with a separate function.
Figure 16B:
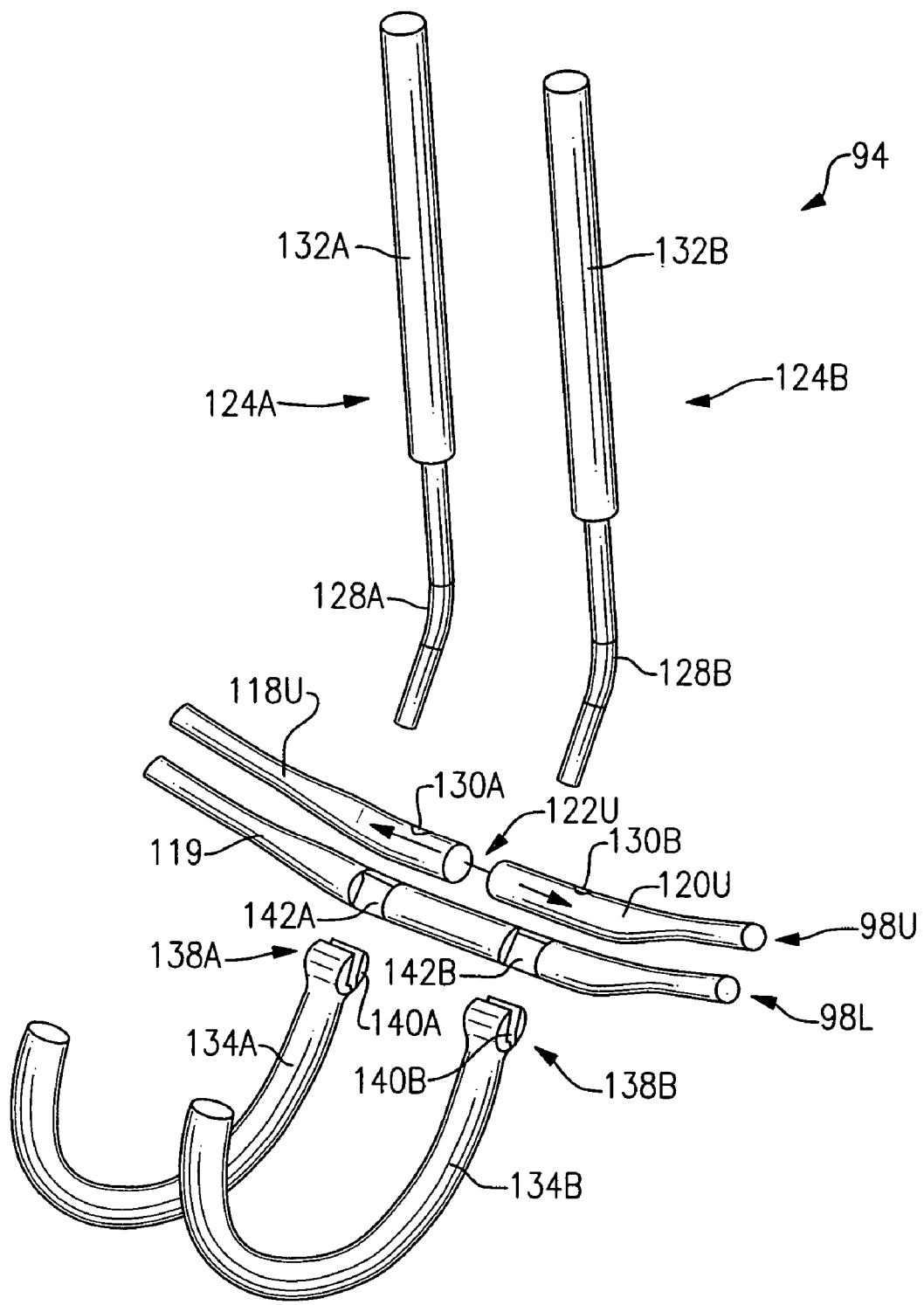
FIG. 16B is a diagrammatic orthogonal view of the alternate cannula assembly for manufacturing a cannula having a pair of separate mouthpieces and a pair of separate nares with each of the mouthpieces and nares having the ability to provide the cannula with a separate function.

Turning now to FIGS. 16A and 16B, these Figures illustrate an alternate embodiment of the cannula mandrel assembly 94 and the nasal cannula 96. As illustrated in those Figures, this alternate embodiment of the nasal cannula 96 and the cannula mandrel assembly 94 has two main body mandrels which define three separate cannula flow paths.

As illustrated in FIG. 16A, the nasal cannula 96 of the present invention includes a nasal main body 98U and a mouth main body 98L in which the nasal main body 98U internally defines a first flow chamber 102U and a second flow chamber 104U which are separated from one another by a dividing wall, a partition or a septum 106U and the mouth main body 98L defines a single lower common third flow chamber 103, without any dividing wall therein, extending from one end of the mouth main body 98L to the opposite end thereof. As shown, nasal main body 98U and mouth main body 98L are arranged parallel with the two main bodies being spaced apart from one another by a sufficiently small distance, for example, 0.1 inch or so, so that the nasal main body 98U and the mouth main body 98L will be joined together and integral formed with one another into a single integral cannula by a waist or web 108 as the septum 106U is formed by the nasal cannula material during the molding, dipping or casting process. As previously described, the nasal cannula material may be, for example, polyvinyl chloride (PVC) or another moltable or castable material, hereafter referred to generally as plastisol.

As also shown, the first flow chamber 102U, the second flow chamber 104U each communicate with a separate exterior opening respectively identified as first port 108U and second port 110U while the single lower common third flow chamber 103 communicates with a pair of opposed exterior openings respectively identified as third port 108L and fourth port 110L. The first and the second flow chambers 102U and 104U are further respectively connected to and communicate with first and second nasal flow chambers 112A and 112B, and the lower common third flow chamber 103 is connected to and communicates with both first and second mouthpiece flow chambers 114A and 114B. The first nasal flow chamber 112A terminates as a first nasal port 113A while the second nasal flow chamber 112B terminates as a second nasal port 113B. The first mouthpiece flow chamber 114A terminates as a first mouth port 115A while the second mouthpiece flow chamber 114B terminates as a second mouth port 115B.

As a consequence, the nasal cannula 96 contains three separate and completely independent internal flow paths. The first flow path 116A comprises the first nasal port 113A, the first nasal flow chamber 112A, the first flow chamber 102U and the first port 108U; the second flow path 116B comprises the second nasal port 113B, the second nasal flow chamber 112B, the second flow chamber 104U and the second port 110U; and the third flow path 116C comprises either the first and/or the second mouth ports 115A and/or 115B and the associated mouthpiece flow chamber 114A and/or 114B, the common third flow chamber 103 and the third port 108L and/or the fourth port 110L.

It will therefore be seen that each of first and second nasal flow chambers 112A and 112B is separately and independently connected to a different one of the first and second ports 108U, 110U, respectively. Both of the first and the second mouthpiece flow chambers 114A and 114B can communicate, via the lower common third flow chamber 103, with either one of the third and fourth ports 108L or 110L. Each of first and second nasal flow chambers 112A and 112B can be separately and both of the mouthpiece flow chambers 114A and 114B together can be thereby connected to a different source of treatment gas, a different monitoring, a different measuring device, etc., thereby allowing additional and more flexible connections to sources of treatment gases, monitoring and measurement devices, etc., and reducing mutual interaction or interference between the gas sources and devices connected to the nasal cannula during use.

Referring now to FIG. 16B and the cannula mandrel assembly 94 for manufacturing the nasal cannula 96, as described herein above the mandrel assembly 94 is manufactured of a material suitable for molding, dipping or casting of the nasal cannula 96. For example, the cannula mandrel assembly 94 may comprise a metal including, but not limited to, steel, aluminum, bronze, brass, copper alloys, beryllium copper, as well as some plastics materials. Beryllium copper is preferred, however, due to its ability to transfer heat rapidly and reliably release the cured PVC, plastisol or other plastics material, herein referred to generally as plastisol.

As illustrated, the mandrel assembly 94 includes first and second nasal main body mandrel sections 118U and 120U for forming the nasal main body 98U and a single mouth main body mandrel 119 for forming the mouth main body 98L. As shown, the first and the second nasal main body mandrel sections 118U and 120L are axially aligned but spaced apart from one another by a small gap 122U in order to form the nasal main body 98U with both the first flow chamber 102U and the second flow chamber 104U separated by the septum 106U, with the septum 106U being formed when the plastisol flows into gap 122U between the two mandrels during the molding, dipping or casting process.

The single mouth main body mandrel 119 is arranged parallel to the first and the second nasal main body mandrel sections 118U and 120U, respectively, but without any small gap separating or dividing the mandrel. It must also be noted that the first and second nasal main body mandrel sections 118U and 120U and the single mouth main body mandrel 119 are spaced apart from one another by a sufficiently small distance, for example, between about 0.03 and about 0.3 inches or so for example, so that the nasal main body 98U and the mouth main body 98L are joined together with one another as a single integral cannula by a waist or web 108 formed by the plastisol flowing between the nasal main body 98U and the mouth main body 98L during the molding, dipping or casting process.

Figure 9:
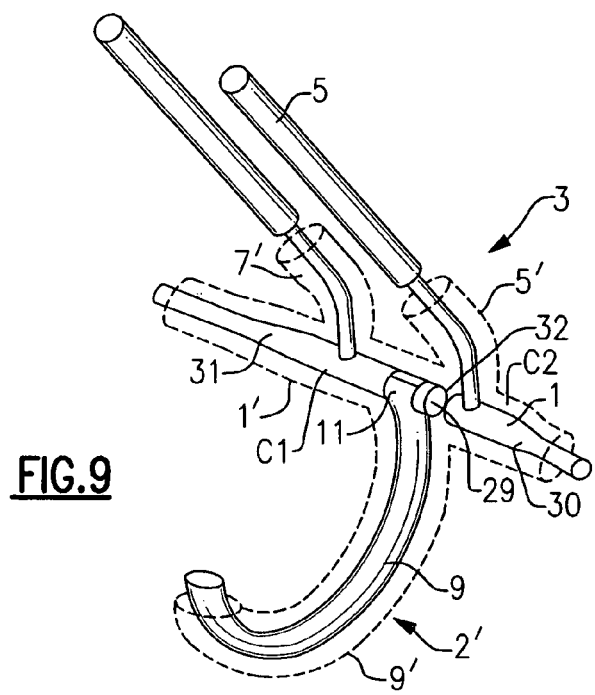
FIG. 9 is an orthogonal view of a cannula mandrel assembly for forming a septum or barrier in a void of the main body forming mandrel, with cannula forming plastics or polymeric material shown in ghost.

The mandrel assembly 94 further includes a pair of nare mandrels 124A and 124B that respectively engage the nasal main body mandrel sections 118U and 120U to facilitate formation of first and second nares 126A and 126B, respectively, of the nasal cannula 96 in which the first nare 126A is formed and shaped so as to extend upward into a first nostril of the patient and define the first nasal port 113A and the first nasal flow chamber 112A and the second nare 126B is formed and shaped so as to extend upward into the other nostril of the patient and define the second nasal port 113B and the second nasal flow chamber 112B. As previously described with reference to FIGS. 1, 2 and 9, for example, each of nare mandrels 124A and 124B has a reduced diameter section 128A, 128B which forms the first and second nares 126A and 126B, respectively, when the cannula forming plastics, polymeric material or plastisol is applied thereto. The reduced diameter sections 128A and 128B of nare mandrels 124A and 124B, respectively, mate with and are received by blind holes 130A and 130B formed in the first and second nasal main body mandrel sections 118U and 120U, respectively, thereby ensuring a continuity of the first and the second nasal flow chambers 112A and 112B with the first flow chamber 102U and the second flow chamber 104U, respectively. The nare mandrels 124A and 124B each also have an enlarged diameter section 132A and 132B which facilitates supporting of the remote free ends of the mandrels in openings of a jig base 146 (see FIG. 17A) during the molding process. Typically, a plurality of identical cannula mandrel assemblies 94 are all sequentially supported by the jig base 146 and simultaneously molded with one another during a batch dipping process. Additionally, the enlarged diameter sections 132A and 132B provide a larger contact surface which facilitates easier gripping of the nare mandrels 124A and 124B when removing the nare mandrels 124A and 124B from the nasal main body mandrel sections 118U and 120U after partial curing of the PVC, plastics material or plastisol on the cannula mandrel assembly 94.

The cannula mandrel assembly 94 further includes the first and the second mouthpiece mandrels 134A and 134B for forming the curved first and second mouthpieces 136A and 136B, respectively, defining the first and second mouth ports 115A and 115B and the first and second mouthpiece flow chambers 114A and 114B, similar to the mouthpieces and mouthpiece mandrels discussed above with reference to FIGS. 1, 2, 3, 4, 5, 6, 9, 10, 11 and 12. Each mouthpiece mandrel 134A, 134B has an end connector 138A and 138B, respectively, for releasably mating the first and second mouthpiece mandrels 134A, 134B with an associated area or section of the single mouth main body mandrel 119 in such a manner as to provide a flow passage between the common third flow chamber 103 of the mouth main body 98L and both the first and the second the mouthpiece flow chambers 114A and 114B.

In the embodiment of end connectors 138A and 138B illustrated in FIG. 16B for example, one end of each end connector 138A, 138B includes a centrally located alignment slot 140A, 140B that engages with a rectangular alignment section 142A, 142B of the corresponding single mouth main body mandrel 119. Each alignment slot 140A, 140B is sized to provide close intimate contact and engagement of the respective alignment slot 140A, 140B with the corresponding rectangular alignment section 142A, 142B which prevents any plastisol from flowing therebetween and removable retains the mouthpiece mandrels 134A, 134B with the single mouth main body mandrel 119 while facilitating removal of the mouthpiece mandrels 134A, 134B from engagement with the single mouth main body mandrel 119 following partial or complete curing of the plastisol on the cannula mandrel assembly 94.

As described above with reference to the embodiments shown in FIGS. 1, 2, 3, 4, 5, 6, 9, 10, 11 and 12, for example, the outer contours of end connectors 138A, 138B are shaped and sized so that the first and second mouthpieces 136A and 136B are effectively continuations of the outer surfaces of mouth main body 98L, will be formed with a substantially uniform thickness of plastisol, will properly align the first and second mouthpieces 136A and 136B in positions shown in FIG. 16A and will facilitate easy withdrawal of mouthpiece mandrels 134A, 134B from the cannula mandrel assembly 94 after molding, dipping or casting of the nasal cannula 96. It should also be noted that the mouthpiece mandrels 134A, 134B may be spaced and oriented sufficiently far from one another, along the single mouth main body mandrel 119, so that mouthpieces 136A and 136B are molded or cast as completely separate elements or, as discussed above with respect to other embodiments, may be sufficiently close to one another so that they are joined together with one another to form an integrated mouthpiece structure having two separate internal flow passages.

It must also be noted that the connection between mouthpiece mandrels 134A and 134B and the single mouth main body mandrel 119 need not be by way of the centrally located alignment slots 140A, 140B engaging the rectangular alignment sections 142A, 142B. The mouthpiece mandrel connections may instead be of the same or similar to the connection between reduced diameter sections 128A and 128B of nare mandrels 124A and 124B with the blind holes 130A and 130B in the first and the second nasal main body mandrel sections 118U and 120U with or without an internal alignment feature or key. It should also be noted that in each instance, the blind holes 130A and 130B may have a tapered internal diameter to provide an interference fit between mouthpiece mandrels 134A and 134B or the reduced diameter sections 128A and 128B of the nare mandrels 124A and 124B and their respective blind holes 130A and 130B as well as associated mating alignment features which assist with proper alignment of the mouthpiece and nare mandrels with the first and second main bodies.

Figure 17B:
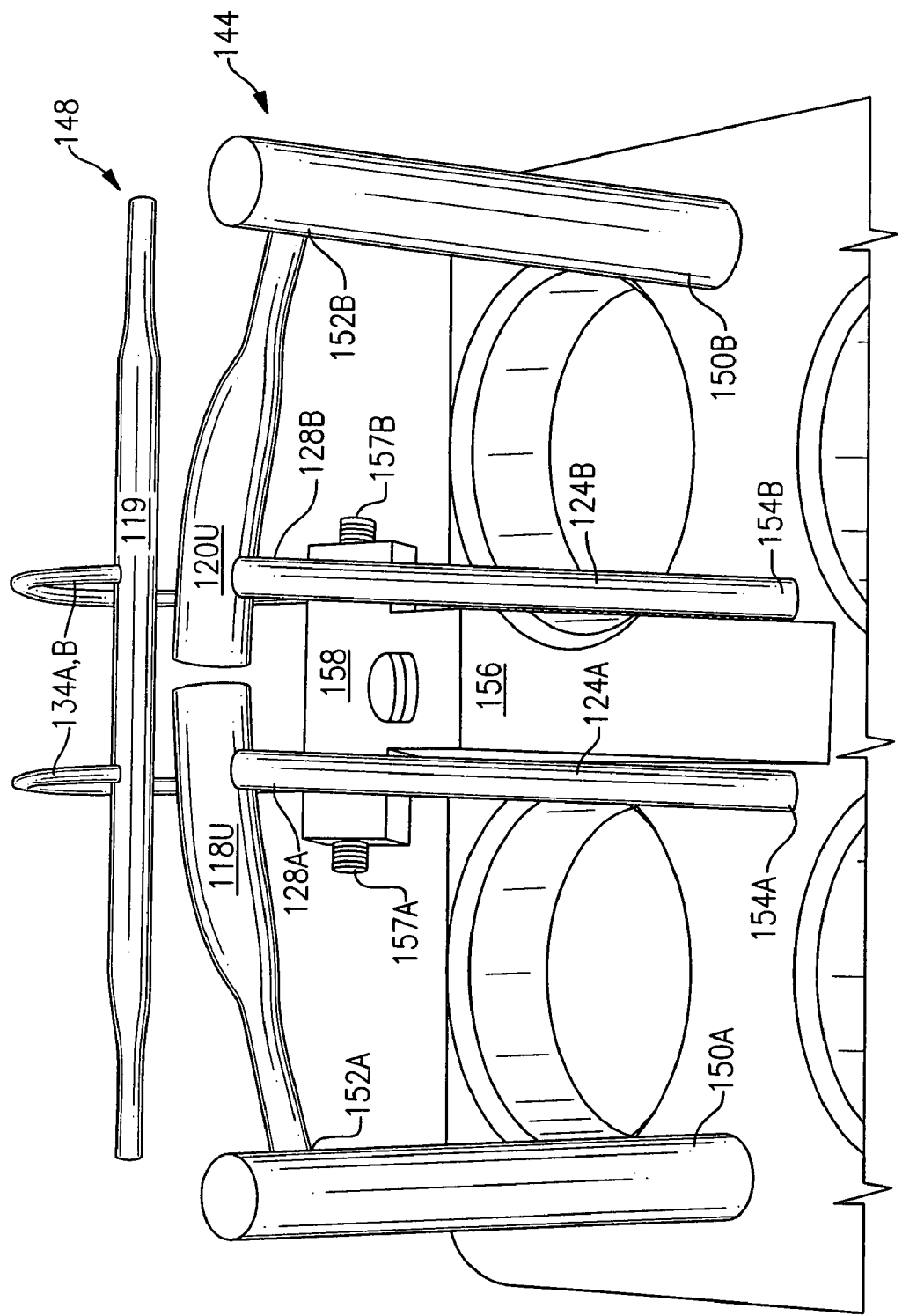
Figure 17C:
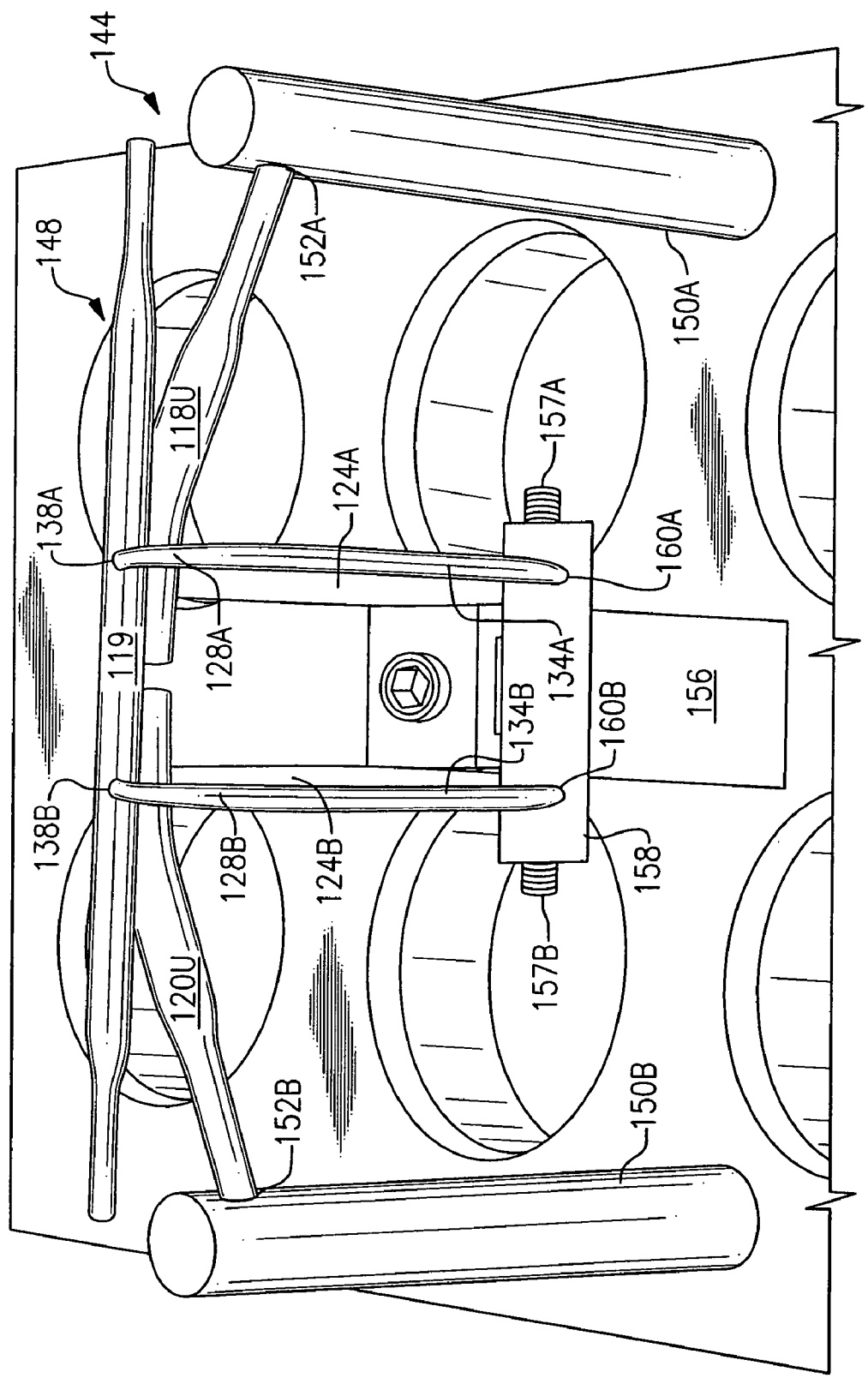
Figure 17D:
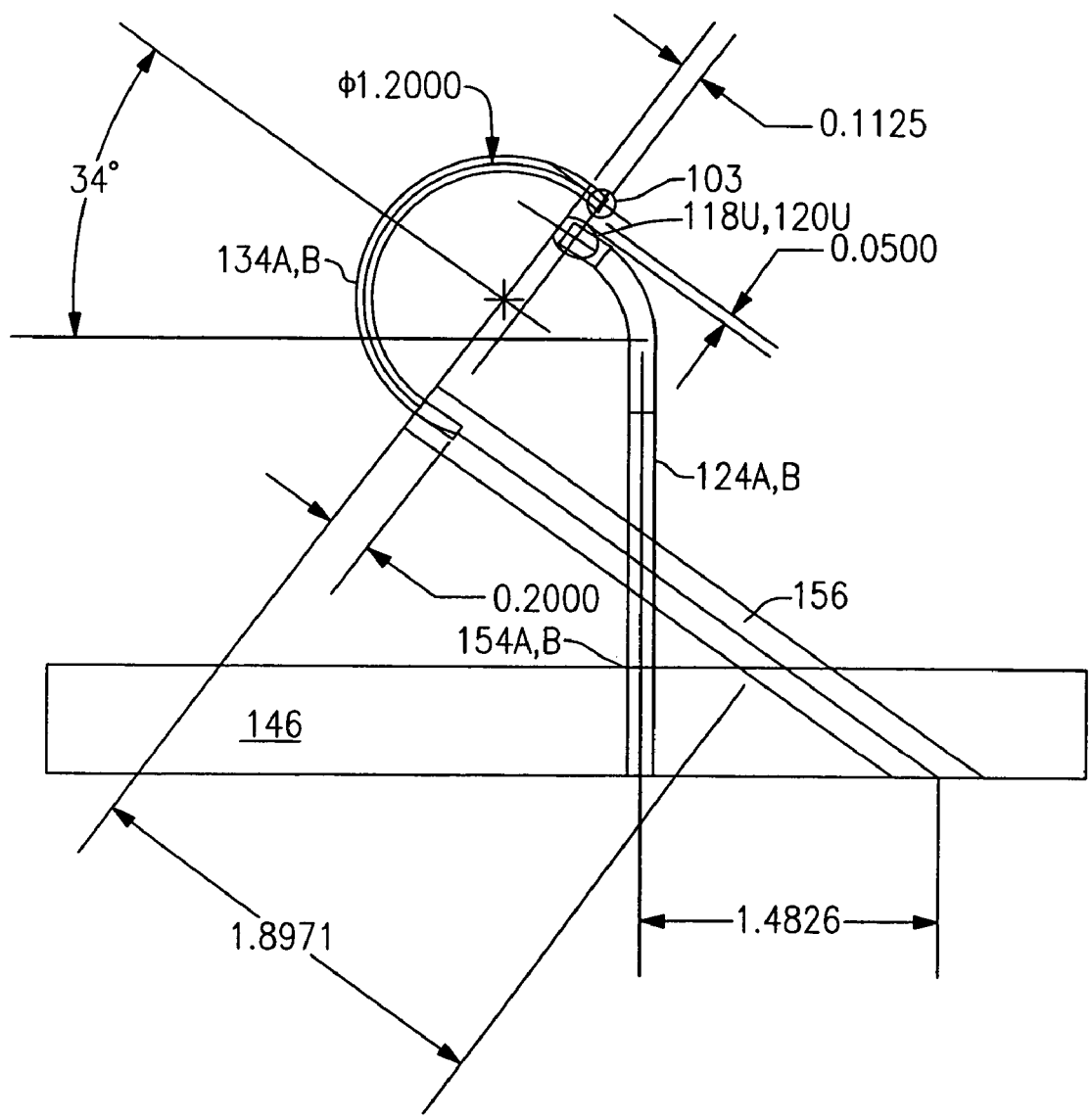

Alternatively, as shown in FIGS. 17A-17C, the mouthpiece mandrels 134A and 134B may extend substantially parallel to one another but the ends of the mouthpiece mandrels 134A and 134B, having the end connectors 138A and 138B respectively, will either bend or curve slightly toward or away from one another. In addition, the single mouth main body mandrel 119 is provided with a pair of blind holes 142A and 142B which have a slightly different (i.e., larger or smaller) spacing than the separation or spacing of the end connectors 138A and 138B so that as the end connectors 138A and 138B are received in the blind holes 142A and 142B, the slight bend or curvature of the mouthpiece mandrels 134A and 134B creates a tension or a compression force which assists with frictionally maintaining the engagement between remote ends of the mouthpiece mandrels 134A and 134B and the single mouth main body mandrel 119 after assembly and during the dipping process.

The molding, dipping or casting process for manufacturing the nasal cannula 96 is the same process as discussed herein above with respect to previous embodiments of the cannula and, as such, need not be described in further detail. It should also be noted that the elements of the cannula mandrel assembly 96 are positioned with respect to one another and supported by the jig base 146 during the molding process, as also described in above and below in further detail. The requirements for supporting the mandrel elements for this embodiment, with respect to one another, are slightly increased over the previous embodiments. As with the previous embodiments, each remote free end of the separate body mandrels 118U, 120U is each supported by a spaced apart upper mandrel support 150A, 150B (see FIG. 17B). However, because the first body mandrel 98U is separate from the mouth main body 98L, an additional support for the mandrels is required. That is, the positioning and orientation of mouthpiece mandrels 134A, 134B and the supported single mouth main body mandrel 119 is generally separately supported.

Figure 16C:
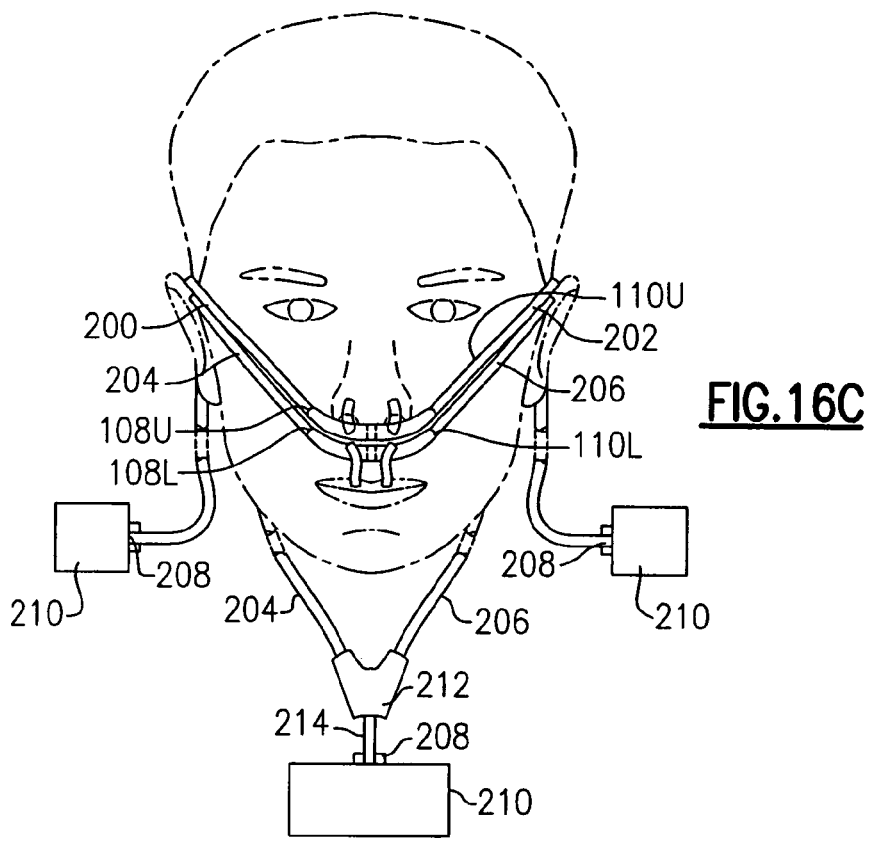
FIG. 16C is a diagrammatic view showing a cannula manufactured form the cannula assembly of FIG. 16B follow addition of flexible conduits and Y-connector to the ports.

Referring now to FIGS. 17A, 17B, 17C and 17D therein are respectively shown an isometric side view, an isometric rear end view, an isometric front end view and a schematic side view of a nare manufacturing jig 144 employing the cannula mandrel assemblies 94 to mold multiple nasal cannula 96, as illustrated in FIGS. 16A and 16C. It will also be appreciated that a somewhat similar nare manufacturing jig 144 may also be employed to mold the nasal cannula 96 discussed below with reference to FIGS. 18A and 18C.

As illustrated therein, the nare manufacturing jig 144 includes a base 146 supporting a plurality of mandrel assembly supports 148, although FIGS. 17A-17C, for purposes of clarity, only show one mandrel assembly support 148 in detail. It must be recognized, in this regard, that the nare manufacturing jig 144 of FIGS. 17A-17C is shown in the mandrel assembly position. That is, during assembly of the various mandrel components with one another on the base 146 or disassembly of the mandrels following manufacture of the cannulas. During the molding process, the nare manufacturing jig 144 is inverted from the assembly position shown in these figures so that the mandrel assembly supports 148 face downward, thereby allowing the mandrel assembly to be dipped into the molten PVC, plastics material or plastisol and thereby completely cover the two main body mandrels and a significant portion of the first and second nare mandrels 124A and 124B and the first and second mouthpieces 136A and 136B in order to form the nasal cannula 96.

As shown, each mandrel assembly support 148 includes a pair of opposed and spaced apart mandrel supports 150A and 150B having opposing upper openings 152A and 152B at their upper portions for receiving the free remote outer ends of the upper first and second nasal main body mandrel sections 118U, 120U. As shown, the mandrel supports 150A and 150B are spaced apart from one another by a distance selected so that when the free remote outer ends of each of the upper first and second nasal main body mandrel sections 118U, 120U engage with their respective upper openings 152A and 152B, the inner adjacent ends of the first and second nasal main body mandrel sections 118U, 120U are located in an opposed and aligned position but spaced apart from one another by a distance sufficient to form a desired wall thickness for the septum 106U. The lower ends of the mandrel supports 150A and 150B are either supported in respective holes or apertures (not separately numbered) formed in the base 146 or integrally formed with the base 146.

Also as shown, each mandrel assembly support 148 further includes lower openings 154A and 154B located in the base 146 for receiving the remote ends of nare mandrels 124A and 124B. Once the remote ends of nare mandrels 124A and 124B are received and located in the lower openings 154A and 154B, the opposite reduced diameter sections 128A and 128B of nare mandrels 124A and 124B will slightly bend or curve away from one another and are located to engage with the blind holes 130A and 130B respectively provided in the first and second nasal main body mandrel sections 118U, 120U. The blind holes 130A and 130B have a slightly different spacing than the spacing of the reduced diameter sections 128A and 128B of the nare mandrels 124A and 124B so that as the reduced diameter sections 128A and 128B are received in blind holes 130A and 130B, the nare mandrels 124A and 124B are biased slightly toward one another and this correction of the slight bend or curvature of the nare mandrels 124A and 124B creates a tension force which assists with frictionally maintaining the engagement between each of the first and second nasal main body mandrel sections 118U, 120U with the respective mandrel support 150A and 150B and the nare mandrel 124A and 124B following completion of assembly and during the dipping process.

It will therefore be recognized that because the upper flow paths 116A and 116B are separate and independent from one another, the mandrel components forming the flow paths 116A and 116B generally are not interconnected with one another to assist in supporting each other. As such, the nare manufacturing jig 144 therefore is constructed to provide dual supports for the mandrel components forming the first and second flow paths 116A and 116B by supporting both opposed ends of the assembled mandrel components forming each of the separate upper flow paths 116A and 116B.

Referring now to the mandrel components forming the curved first and second mouthpieces 136A and 136B, it will be recognized that the mandrel components for forming the mouthpieces 136A and 136B together form a single flow passage, as described above. As a result, the mandrel components forming mouthpieces 136A and 136B, that is, the single mouth main body mandrel 119 and the mouthpiece mandrels 134A and 134B, are assembled with one another as a single unit in which the component parts assist with supporting and aligning one another. As a result, the nare manufacturing jig 144 includes a centrally located fixed position post 156 and a supported adjustable positioning bar 158 secured by a set screw. The positioning bar 158 extends generally parallel to and is spaced from the desired location of the single mouth main body mandrel 119 and includes a pair of spaced apart bar openings 160A and 160B for closely receiving the corresponding outer ends of mouthpiece mandrels 134A and 134B. A respective set screw 157A, 157B, in opposed ends of the positioning bar 158, allows release attachment and some adjustment of the relative positions of the end connectors 138A, 138B of the mouthpiece mandrels 134A and 134B with respect to the positioning bar 158. When desired, the ends of the mouthpiece mandrels 134A and 134B are engaged with positioning bar 158 and with the single mouth main body mandrel 119, the positions of the mouthpiece mandrels 134A and 134B may be adjusted so that the single mouth main body mandrel 119 is supported parallel to first and second nasal main body mandrel sections 118U, 120U and spaced apart therefrom by the distance necessary to form the web 108 joining the nasal main body 98U and the mouth main body 98L with one another as a single integral cannula.

Lastly, it should be noted that the nare manufacturing jig 144 shown in FIGS. 17A-17D can be readily adapted to the manufacture of the cannula nare 96 as shown and described with reference to FIGS. 18A and 18B. For example, in the cannula 96 of FIGS. 18A and 18B, the mouth main body 98L is formed as two separate mandrel sections 118L, 120L separated from one another by a gap 122L, as is the case with the nasal main body mandrel sections 118U, 120U. In this embodiment, each cannula mandrel assembly 94 could, for example, include an additional pair of mandrel supports (not shown—similar to mandrel supports 150A and 150B) also having opposing upper openings in their upper portions for receiving, positioning and supporting the remote ends of the first and second mouth main body mandrel sections 118L and 120L in the same manner as the first and second nasal main body mandrels 118U, 120U are supported, as discussed above, or the mandrel supports 150A and 150B may be modified and provided with an additional pair of opposing upper openings for supporting the remote ends of the first and second mouth main body mandrel sections 118L and 120L.

Figure 18C:
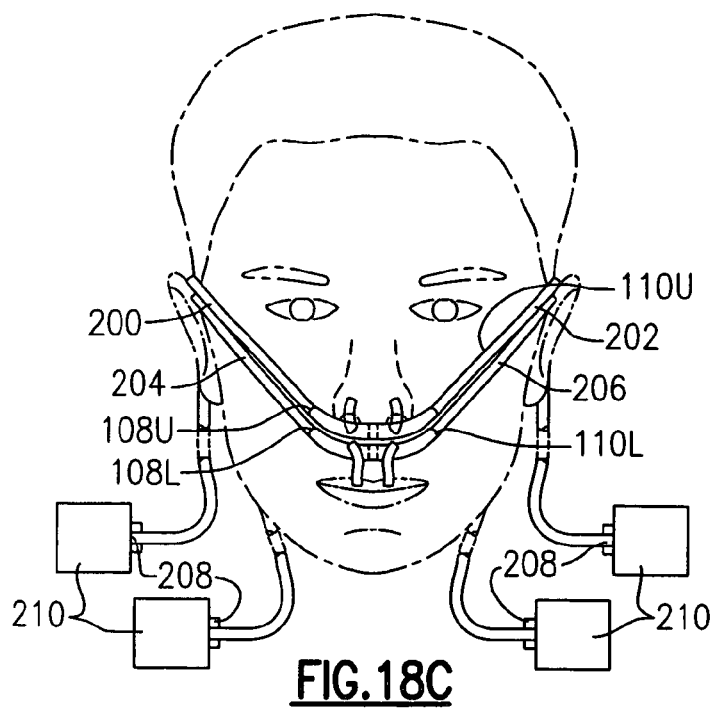
FIG. 18C is a diagrammatic view showing a cannula manufactured form the cannula assembly of FIG. 18B follow addition of flexible conduits to the ports.

It is sometime necessary or desirable to have still another separate and independent external connection with the nasal cannula with still another corresponding separate and independent flow path within the nasal cannula. A nasal cannula, according to the present invention and providing such additional external connection and internal flow path, is illustrated in FIGS. 18A, 18B and 18C and described below. FIG. 18A illustrates a cannula mandrel assembly 94 employed in molding the nasal cannula 96 with the nasal cannula 96 shown in ghost form on the mandrel assembly 94, during the latter stages of the molding of the nasal cannula 96, while FIG. 18B illustrates mandrel assembly 94 alone.

Figure 18A:
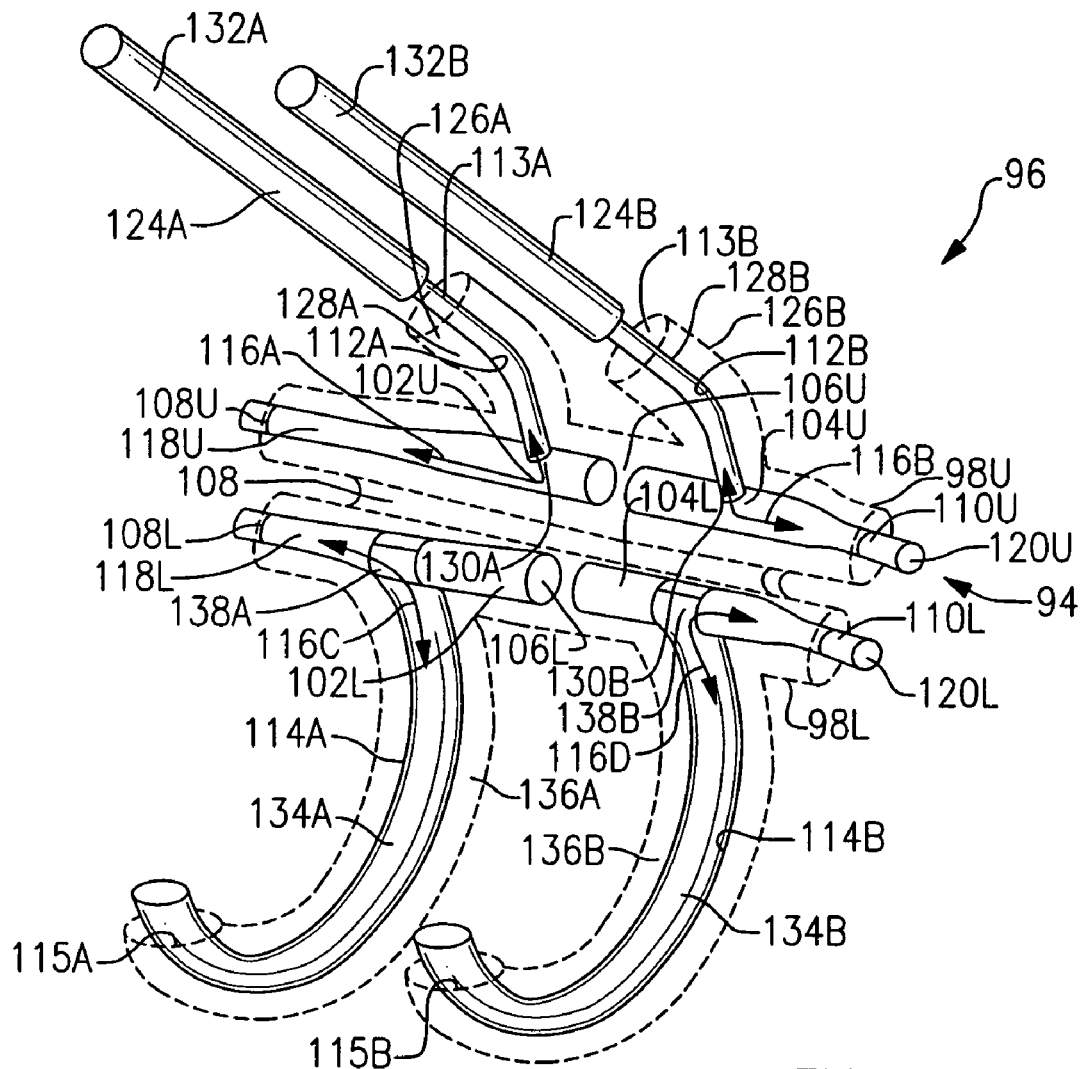
FIG. 18A is a diagrammatic orthogonal view of a cannula assembly, with a manufacture cannula shown in dashed lines, in which the cannula has a pair of separate mouthpieces and a pair of separate nares with each of the mouthpieces and nares having the ability to provide the cannula with a separate function.

As illustrated in FIG. 18A, the nasal cannula 96 of the present invention includes a nasal main body 98U and a substantially axially aligned mouth main body 98L. The nasal main body 98U comprises a first flow chamber 102U and a second flow chamber 104U separated by a nasal septum 106U and the first second body 98L comprises a third flow chamber 102L and a fourth flow chamber 104L separated by a mouth septum 106L. As shown, nasal main body 98U and the mouth main body 98L are parallel and spaced apart from one another by a sufficiently small distance, for example, 0.1 inch or so, so that nasal main body 98U and the mouth main body 98L are joined together into a single integral cannula by a waist or web 108, formed by the nasal cannula material, during the molding, dipping or casting process. As previously described, the nasal cannula material may be, for example, polyvinyl chloride (PVC) or another moltable or castable material, hereafter referred to generally as plastisol.

As also shown, the first flow chamber 102U, the second flow chamber 104U, the third flow chamber 102L and the fourth flow chamber 104L each communicate with only a single exterior opening or port, respectively identified as first port 108U, second port 110U, third port 108L and fourth port 110L, located at the outer end of the respective flow chambers 102L, 104L, 102U and 104U. The first and second flow chambers 102U and 104U are further respectively connected to first and second nasal flow chambers 112A and 112B, and third and fourth flow chambers 102L and 104L are respectively connected to first and second mouthpiece flow chambers 114A and 114B. The first nasal flow chamber 112A terminates as a first nasal port 113A while the second nasal flow chamber 112B terminates as a second nasal port 113B. The first mouthpiece flow chamber 114A terminates as a first mouth port 115A while the second mouthpiece flow chamber 114B terminates as a second mouth port 115B.

As a consequence, the nasal cannula 96 contains four separate and completely independent flow paths, each being connected to a separate exterior inlet/outlet or port. The first flow path 116A comprises the first nasal port 113A, the first nasal flow chamber 112A, the first flow chamber 102U and the first port 108U; the second flow path 116B comprises the second nasal port 113B, the second nasal flow chamber 112B, the second flow chamber 104U and the second port 110U; the third flow path 116C comprises the first mouth port 115A, the first mouthpiece flow chamber 114A, the third flow chamber 102L and the third port 108L; and the fourth flow passage 116D comprises the second mouth port 115B, the second mouthpiece passage 114B, the fourth flow chamber 104L and the fourth port 110L.

It will therefore be seen that each of the first and second nasal flow chambers 112A and 112B and each of the first and second mouthpiece flow chambers 114A and 114B is separately and independently connected to a completely separate and distinct inlet/outlet, namely, first port 108U, third port 108L, second port 110U or fourth port 110L, respectively. Each of the first and second nasal flow chambers 112A and 112B and each of first and second mouthpiece flow chambers 114A and 114B can thereby be connected to a different source of treatment gas, a different monitoring device, a different measuring device, etc., thereby allowing additional and more flexible connections to various sources of treatment gases and/or different monitoring and measurement devices and reducing mutual interaction or interference between the gas sources and devices connected to the nasal cannula.

Referring now to the cannula mandrel assembly 94 for the nasal cannula 96, as described herein above the mandrel assembly 94 is manufactured of a material suitable for molding, dipping or casting of the nasal cannula 96. For example, the cannula mandrel assembly 94 may comprise a metal including, but not limited to, steel, aluminum, bronze, brass, copper alloys, beryllium copper, as well as some plastics materials. Beryllium copper is preferred, however, due to its ability to transfer heat rapidly and reliably release the cured PVC, plastisol or other plastics material, herein referred to generally as plastisol.

As illustrated, the mandrel assembly 94 includes first and second nasal main body mandrel sections 118U and 120U for forming a nasal main body 98U and first and second mouth main body mandrel sections 118L and 120L for forming a mouth main body 98L. As shown, the first and the second nasal main body mandrel sections 118U and 120L are axially aligned but spaced apart from one another by a small gap 122U in order to form the nasal main body 98U with the first flow chamber 102U and the second flow chamber 104U separated from one another by a septum 106U with the septum 106U being formed when the plastisol flows into gap 122U during the molding or dipping process. In a like manner, the first and the second mouth main body mandrel sections 118L and 120L are arranged parallel to the first and the second nasal main body mandrel sections 118U and 120U, respectively, and are axially aligned but axially spaced apart from one another by a small gap 122L to form the mouth main body 98L with the third flow chamber 102L and the fourth flow chamber 104L separated from one another by a septum 106L, again with the septum 106L being formed when the plastisol flows into gap 122L during the molding, dipping or casting process. It must also be noted that the first and second nasal main body mandrel sections 118U and 120U and the first second mouth main body mandrel sections 118L and 120L are arranged parallel to and spaced apart from one another by a sufficiently small distance, for example, between about 0.03 and about 0.3 inches or so, so that the nasal main body 98U and the mouth main body 98L are joined together with one another into a single integral cannula by a waist or web 108 formed by the plastisol flowing between the nasal main body 98U and the mouth main body 98L during the molding, dipping or casting process.

The mandrel assembly 94 further includes a pair of nare mandrels 124A and 124B that respectively engage the nasal main body mandrel sections 118U and 120U to facilitate formation of first and second nares 126A and 126B, respectively, of the nasal cannula 96 in which the first nare 126A is formed and shaped so as to extend upward into a first nostril of the patient and define the first nasal port 113A and the first nasal flow chamber 112A and the second nare 126B is formed and shaped so as to extend upward into the other nostril of the patient and define the second nasal port 113B and the second nasal flow chamber 112B. As previously described with reference to FIGS. 1, 2 and 9, for example, each of nare mandrels 124A and 124B has a reduced diameter section 128A, 128B which forms the first and second nares 126A and 126B, respectively, when the cannula forming plastics, polymeric material or plastisol is applied thereto. The reduced diameter sections 128A and 128B of nare mandrels 124A and 124B, respectively, mate with and are received by blind holes 130A and 130B formed in the first and second nasal main body mandrel sections 118U and 120U, respectively, thereby ensuring a continuity of the first and the second nasal flow chambers 112A and 112B with the first flow chamber 102U and the second flow chamber 104U, respectively.

The nare mandrels 124A and 124B each also have an enlarged diameter section 132A and 132B which facilitates supporting of the remote free ends of the mandrels in openings of a jig base 146 (see FIG. 17A) during the molding process. Typically, a plurality of identical cannula mandrel assemblies 94 are all sequentially supported by the jig base 146 and simultaneously molded with one another during a batch dipping process. Additionally, the enlarged diameter sections 132A and 132B provide a larger contact surface which facilitates easier gripping of the nare mandrels 124A and 124B when removing the nare mandrels 124A and 124B from the nasal main body mandrel sections 118U and 120U after partial curing of the PVC, plastics material or plastisol on the cannula mandrel assembly 94.

The cannula mandrel assembly 94 further includes the first and the second mouthpiece mandrels 134A and 134B for forming the curved first and second mouthpieces 136A and 136B, respectively, defining the first and second mouth ports 115A and 115B and the first and second mouthpiece flow chambers 114A and 114B, similar to the mouthpieces and mouthpiece mandrels discussed above with reference to FIGS. 1, 2, 3, 4, 5, 6, 9, 10, 11 and 12. Each mouthpiece mandrel 134A, 134B has an end connector 138A and 138B, respectively, for mating the first and second mouthpiece mandrels 134A, 134B with the first and second mouth main body mandrel sections 118L and 120L, respectively, in such a manner as to provide a continuous flow passage between the third and the fourth flow chambers 102L and 104L and the first and the second mouthpiece flow chambers 114A and 114B, respectively.

Figure 18B:
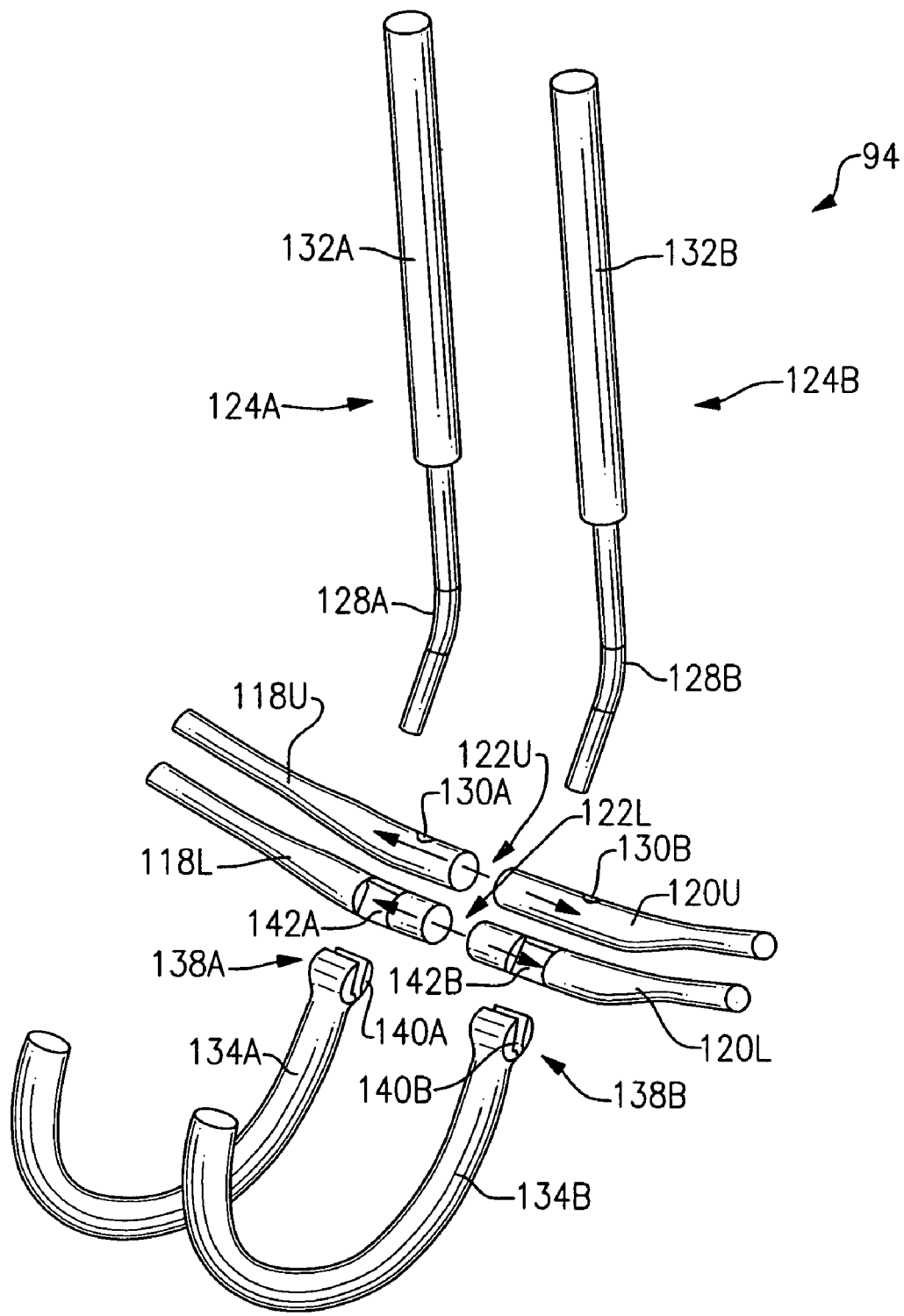
FIG. 18B is a diagrammatic orthogonal view of a cannula assembly for manufacturing a cannula having a pair of separate mouthpieces and a pair of separate nares with each of the mouthpieces and nares having the ability to provide the cannula with a separate function.

In the embodiment of the end connectors 138A and 138B illustrated in FIGS. 18A and 18B, one end of each end connector 138A, 138B includes a centrally located alignment slot 140A, 140B that engages with a rectangular alignment section 142A, 142B of the corresponding mouth main body mandrel 118L, 120L. Each alignment slot 140A, 140B is sized to provide close intimate contact and engagement of the alignment slot 140A, 140B with the corresponding rectangular alignment section 142A, 142B which prevents any plastisol from flowing therebetween and removable retains the mouthpiece mandrel 134A, 134B with the corresponding mouth main body mandrel section 118L, 120L while, at the same time, facilitating removal of the mouthpiece mandrels 134A, 134B from engagement with the mouth main body mandrel sections 118L, 120L following partial or complete curing of the plastisol on the cannula mandrel assembly 94.

As described above with reference to the embodiments shown in FIGS. 1, 2, 3, 4, 5, 6, 9, 10, 11 and 12, for example, the outer contours of end connectors 138A, 138B are shaped and sized so that the first and second mouthpieces 136A and 136B are effectively continuations of the outer surfaces of the mouth main body 98L, will be formed with a substantially uniform thickness of plastisol, will properly align the first and second mouthpieces 136A and 136B to extend as shown in FIG. 18A and will facilitate withdrawal of mouthpiece mandrels 134A, 134B from the cannula mandrel assembly 94 following molding, dipping or casting of the nasal cannula 96. It should also be noted that the mouthpiece mandrels 134A, 134B may be respectively coupled to the mouth main body mandrel sections 118L, 120L either sufficiently spaced apart from one another and oriented with respect to one another so that mouthpieces 136A and 136B are molded or cast as completely separated elements or, as discussed above with respect to other embodiments, may be located sufficiently close to one another to be joined with one another and form an integrated mouthpiece structure still having two separate flow passages.

The molding, dipping or casting process for making the nasal cannulas 96 is the same process as discussed herein above with respect to other embodiments of the cannula of the present invention and, as such, is not described in further detail. It should also be noted that the elements of the cannula mandrel assembly 96 are positioned with respect to one another and supported by the jig base 146 during the molding process, as also described in detail above. The requirements for supporting the mandrel elements with respect to one another are somewhat increased, however, because both the nasal and the mouth main body mandrel sections of the cannula are formed by four separate and independent main body mandrels 118U, 120U, 118L and 120L, rather than two or three main body mandrel sections as with the previous embodiments. The molding jig would therefore be required to support the outer remote free ends of all four of the main body mandrel sections 118U, 120U, 118L and 120L, as briefly discussed above, in the correct orientations and positions. As discussed briefly above, the remote free ends of the nasal and the mouth main body mandrel sections 118L, 118U would engage with and be releasably supported by possibly a single mandrel support or possibly two adjacent mandrel supports (not shown) both fixedly attached to the base 146. The remote free ends of the second nasal and mouth main body mandrel sections 120U, 120L would engage with and be releasably supported by an opposed single mandrel support or two adjacent mandrel supports (not shown) also fixedly attached to the base 146. The adjacent ends of the nasal and the mouth main body mandrel sections 118L, 118U would engage with and be releasably supported by of the first nare mandrel 124A and the first mouthpiece mandrel 134A, as discussed above. The remote free ends of the second nasal and mouth main body mandrel sections 120U, 120L would engage with and be releasably supported by the second nare mandrel 124B and the second mouthpiece mandrel 134B, supported by the base 146.

Alternatively, as shown in FIGS. 17A-17C, the mouthpiece mandrels 134A and 134B may extend substantially parallel to one another but the ends of the mouthpiece mandrels 134A and 134B, having the substantially cylindrical end connectors 138A and 138B respectively, will either bend or curve slightly toward or away from one another. In addition, the first and second mouth main body mandrel sections 118L, 120L are each provided with a blind hole 142A or 142B. The spacing or separation of the blind holes 142A and 142B is slightly different (i.e., larger or smaller) than the separation or spacing of the end connectors 138A and 138B so that as the end connectors 138A and 138B are received in and engage with the blind holes 142A and 142B, the slight bend or curvature of the mouthpiece mandrels 134A and 134B creates a tension or a compression force which assists with frictionally maintaining the engagement between remote ends of the mouthpiece mandrels 134A and 134B and the first and second mouth main body mandrel sections 118L, 120L after assembly and during the dipping process.

It should be recognized that other alignment mechanisms may be advantageous employed with respect to the orientation and positioning of the first and nare mandrels 124A, 124B with respect to the nasal main body mandrels 118U, 120U and the mouthpiece mandrels 134A and 134B with respect to the first and second mouth main body mandrel sections 118L, 120L.

It must also be recognized that a variety of end connector 138A, 138B and mating alignment sections 142A, 142B may be employed. For example, the ends of mouthpiece mandrels 134A, 134B engaging mouth main body mandrel sections 118L, 120L or the ends of nare mandrels 124A, 124B engaging nasal main body mandrel sections 118U, 120U, or both, may be non-rotatably keyed, by, for example, end portions having square or rectangular cross-sections, to engage correspondingly shaped opening or holes in nasal and mouth main body mandrel sections 118U, 120U, 118L and 120L. It should also be recognized that the design of the attachments of the mouthpiece mandrels 134A, 134B or the nare mandrels 124A, 124B to the mouth main body mandrel sections 118L, 120L or the nasal main body mandrels 118U, 120U may effect the design of the jig supporting and locating the mandrel elements during the casting or molding process. That is, if the temporary attachments between mouthpiece mandrels 134A, 134B or nare mandrels 124A, 124B and main body mandrel sections 118L, 120L, 118U, 120U are sufficiently secure and sufficiently precise to provide the required degree of orientation and positioning, the jig many support and manipulate mandrel assembly 94 by means of the outer ends of may be supported and manipulated by the outer ends of mouthpiece mandrels 134A, 134B and nare mandrels 124A, 124B. That is, the main body mandrels 118U, 118L, 120U and 120L become the dependent elements supported by mouthpiece mandrels 134A, 134B and nare mandrels 124A, 124B.

As shown in FIG. 18C, each one of the first ports 108U, the second ports 10U, the third ports 108L and the fourth ports 110L of the nasal cannula 96 is bonded or otherwise permanently connected, in a conventional manner, with a respective first end of a flexible plastic or PVC tubing or conduit 200, 202, 204, 206. The remote opposed end of each PVC tubing or flexible conduit 200, 202, 204, 206 is integrally joined, bonded or otherwise permanently connected with a conventional end coupling or a proprietary end connector 208 to facilitate connection of that end of the tubing or conduit with a desired device 210, such as a desired gas supply device, a desired monitoring device, a desired detection device, etc., (only diagrammatically shown). With respect to the flexible tubing or conduit which is coupled to the opposed ends of the third and fourth ports 108L, 110L that communicate with the common chamber of the mouth main body (FIG. 16C), typically the remote free ends of the two flexible tubings or conduits 204, 206 connected thereto are joined with one another, via conventional Y-connector 212, and a first end of a further single flexible tubing or conduit 214 is permanently connected to an opposite end of the conventional Y-connector 212 and the remote free end of the single flexible tubing or conduit 214 is integrally joined, bonded or otherwise permanently connected with a conventional coupling or a proprietary end connector 208 to facilitate connection of that end of the flexible tubing or conduit 214 with a desired device 210, such as a desired gas supply device, a desired monitoring device, a desired detection device, etc., (only diagrammatically shown).

Since certain changes may be made in the above described improved cannula and method of manufacturing the same, without departing from the spirit and scope of the invention herein involved, it is intended that all of the subject matter of the above description or shown in the accompanying drawings shall be interpreted merely as examples illustrating the inventive concept herein and shall not be construed as limiting the invention.

We claim:

1. A cannula having at least three completely separate flow passages, the cannula comprising:
    a nasal main body having first and second main flow chambers respectively communicating with first and second ports, and the first and second main flow chambers being separated from one another by a nasal septum;
    a mouth main body located adjacent the nasal main body and having at least a third main flow chamber therein communicating with at least third port, and the third main flow chamber being completely separate from both the first and the second main flow chambers;
    a first nare having a first nasal port and a first nasal flow chamber communicating with the first main flow chamber;
    a second nare having a second nasal port and a second nasal flow chamber communicating with the second main flow chamber;
    a first mouthpiece having a first mouth port and a first mouthpiece flow chamber communicating with the third main flow chamber; and
        a first flow path comprises the first port, the first main flow chamber the first nasal flow chamber and the first nasal port;
        a second flow path comprises the second port, the second main flow chamber, the second nasal flow chamber and the second nasal port; and
        a third flow path comprises the third port, the third main flow chamber, the first mouthpiece flow chamber and the first mouth port.

2. The cannula according to claim 1, the cannula includes a second mouthpiece which has a second mouth port and a second mouthpiece flow chamber which also communicate with the third main flow chamber and the third main flow chamber has a fourth port, located opposite the third port, which also communicates with the third flow chamber.

3. The cannula according to claim 1, wherein a first flexible conduit is connected to the first port, a second flexible conduit is connected to the second port, a third flexible conduit is connected to the third port third and opposed ends of the first, the second and the third flexible conduits each has a coupling facilitating connection to a desired device.

4. The cannula according to claim 3, wherein a fourth flexible conduit is connected to the fourth port and remote ends of the third and fourth ports are connected to a Y-connector and a remote end of the Y-connector has a coupling facilitating connection to a desired device.

5. The cannula according to claim 3, wherein the desired device is one of a device for monitor breathing of a patient, a device sampling end tidal $CO_2$ content in an exhaled breath of a patient to determine the patient's blood $CO_2$ concentration level, a device for supplying a treating gas to the patient, and a device for detection of apnea of a patient.

6. The cannula according to claim 1, wherein the cannula includes a second mouthpiece which has a second mouth port and a second mouthpiece flow chamber therein;
    the mouth main body is separated by a mouth septum into the third main flow chamber and a fourth main flow chamber with the fourth main flow chamber communicating with a fourth port; and
    the cannula defines a fourth flow path which comprises the fourth port, the fourth main flow chamber, the second mouthpiece flow chamber and the second mouth port.

7. The cannula according to claim 6, wherein a first flexible conduit is connected to the first port, a second flexible conduit is connected to the second port, a third flexible conduit is connected to the third port and a fourth flexible conduit is connected to the fourth port, and opposed ends of the first, the second, the third and the fourth flexible conduits each has a coupling facilitating connection to a desired device.

8. The cannula according to claim 7, wherein the desired device is one of a device for monitor breathing of a patient, a device sampling end tidal $CO_2$ content in an exhaled breath of a patient to determine the patients blood $CO_2$ concentration level, a device for supplying a treating gas to the patient, and a device for detection of apnea of a patient.

9. A method of manufacturing a cannula having at least three completely separate flow passages, the method comprising the steps of:
    forming a nasal main body with first and second main flow chambers respectively communicating with first and second ports, and separating the first and second main flow chambers from one another by a nasal septum;
    locating a mouth main body adjacent to and spaced apart from the nasal main body and forming at least a third main flow chamber therein communicating with at least a third port, and completely separating thr third main flow chamber from both the first and the second main flow chambers;
    forming a first nare with a first nasal port and a first nasal flow chamber communicating with the first main flow chamber;
    forming a second nare with a second nasal port and a second nasal flow chamber communicating with the second main flow chamber;
    forming a first mouthpiece with a first mouth port and a first mouthpiece flow chamber communicating with the third main flow chamber, and the first main flow chamber, the second main flow chamber and the third main flow chamber each being independent from one another; and
    forming a first flow path comprising the first port, the first main flow chamber, the first nasal flow chamber and the first nasal port;
    forming a second flow path comprising the second port, the second main flow chamber, the second nasal flow chamber and the second nasal port; and
    forming a third flow path comprising the third port, the third main flow chamber and the first mouthpiece flow chamber.

10. The method of manufacturing a cannula according to claim 9, further comprising the steps of providing the cannula with a second mouthpiece which has a second mouth port and a second mouthpiece flow chamber which communicate with the third main flow chamber, and providing the third main flow chamber with a fourth port, located opposite the third port, which also communicates with the third main flow chamber.

11. The method of manufacturing a cannula according to claim 9, further comprising the steps of connecting a first flexible conduit to the first port, connecting a second flexible conduit to the second port, connecting a third flexible conduit to the third port and attaching a coupling to opposed ends of the first, the second and the third flexible conduits to facilitate connection thereof to a desired device.

12. The method of manufacturing a cannula according to claim 11, further comprising the steps of connecting a fourth flexible conduit to the fourth port and connecting remote ends of the third and fourth conduits to a Y-connector and attaching a coupling to a remote end of the Y-connector to facilitate connection thereof to a desired device.

13. The method of manufacturing a cannula according to claim 11, further comprising the steps of using one of a device for monitor breathing of a patient, a device sampling end tidal $CO_2$ content in an exhaled breath of a patient to determine the patient's blood $CO_2$ concentration level, a device for supplying a treating gas to the patient, and a device for detection of apnea of a patient as the desired device.

14. The method of manufacturing a cannula according to claim 9, further comprising the steps of providing the cannula with a second mouthpiece which has a second mouth port and a second mouthpiece flow chamber therein;
separating the mouth main body by a mouth septum into the third main flaw chamber and a fourth main flow chamber with the fourth main flow chamber communicating with a fourth port; and
defining within the cannula a fourth flow path which comprises the fourth port, the fourth main flow chamber, the second mouthpiece flow chamber and the second mouth port.

15. The method of manufacturing a cannula according to claim 14, further comprising the steps of connecting a first flexible conduit to the first port, connecting a second flexible conduit to the second port, connecting a third flexible conduit to the third port third and connecting a fourth flexible conduit to the fourth port, and providing opposed ends of the first, the second, the third and the fourth flexible conduits with a coupling which facilitates connection thereof to a desired device.

16. The method of manufacturing a cannula according to claim 15, further comprising the steps of using one of a device for monitor breathing of a patient, a device sampling end tidal $CO_2$ content in an exhaled breath of a patient to determine the patient's blood $CO_2$ concentration level, a device for supplying a treating gas to the patient, and a device for detection of apnea of a patient as the desired device.

17. A cannula mandrel assembly for manufacturing a nasal cannula having at least three completely separate flow paths, the cannula mandrel assembly comprising:
axially aligned and spaced apart first and second nasal main body mandrel sections form forming first and second main flow chambers which are separated from one another by a nasal septum;
a mouth main body mandrel located adjacent to and spaced apart from the first and second nasal main body mandrel sections for forming a third main flow chamber which is completely separate from both the first and the second main flow chambers;
first and second nare mandrels respectively connected with and extending from the first and second nasal main body mandrel sections; and
at least a first mouthpiece mandrel extending from the mouth main body mandrel.

18. The cannula mandrel assembly according to claim 17, wherein the mouth main body mandrel comprises separate first and second mouth nasal main body mandrel sections, and the first mouthpiece mandrel is connected to the first mouth main body mandrel section and the second mouthpiece mandrel is connected to the second mouth main body mandrel section.

* * * * *